(12) United States Patent
Pitzalis

(10) Patent No.: US 9,416,174 B2
(45) Date of Patent: Aug. 16, 2016

(54) ANTIBODY SPECIFICALLY BINDING SYNOVIAL MICROVASCULATURE OF ARTHRITIS PATIENTS

(75) Inventor: Constantino Pitzalis, London (GB)

(73) Assignee: QUEEN MARY AND WESTFIELD COLLEGE UNIVERSITY OF LONDON, London (GB)

( * ) Notice: Subject to any disclaimer, the term of this patent is extended or adjusted under 35 U.S.C. 154(b) by 377 days.

(21) Appl. No.: 13/877,097

(22) PCT Filed: Sep. 30, 2011

(86) PCT No.: PCT/GB2011/051854
§ 371 (c)(1),
(2), (4) Date: Jun. 25, 2013

(87) PCT Pub. No.: WO2012/042270
PCT Pub. Date: Apr. 5, 2012

(65) Prior Publication Data
US 2013/0266587 A1    Oct. 10, 2013

(30) Foreign Application Priority Data
Sep. 30, 2010    (GB) .................................. 1016494.5

(51) Int. Cl.
| C07K 16/00 | (2006.01) |
| C07K 16/46 | (2006.01) |
| A61K 39/395 | (2006.01) |
| A61K 39/44 | (2006.01) |
| C07K 16/18 | (2006.01) |
| C07K 16/28 | (2006.01) |

(52) U.S. Cl.
CPC ................. *C07K 16/18* (2013.01); *C07K 16/28* (2013.01); *C07K 2317/21* (2013.01); *C07K 2317/622* (2013.01)

(58) Field of Classification Search
None
See application file for complete search history.

(56) References Cited

U.S. PATENT DOCUMENTS

| 5,859,205 A * | 1/1999 | Adair ...................... C07K 16/18 530/387.1 |
| 2005/0158321 A1 | 7/2005 | Hurez et al. |
| 2009/0098536 A1* | 4/2009 | Schett .................. C12Q 1/6883 435/6.18 |

FOREIGN PATENT DOCUMENTS

| WO | WO-90/05144 A1 | 5/1990 |
| WO | WO-03/002609 A2 | 1/2003 |
| WO | WO2006017538 | * 2/2006 |
| WO | WO-2009/067820 A1 | 6/2009 |

OTHER PUBLICATIONS

Ozerdem et al. Pathological angiogenesis is reduced by targeting pericytes via the NG2 proteoglycan. Angiogenesis. 2004; 7(3): 269-276.*
Klimka et al.,Human anti-CD30 recombinant antibodies by guided phage antibody selection using cell panning. British Journal of Cancer (2000) 83:252-260.*
Paul, Fundamental Immunology, 3rd Edition, 1993, pp. 292-295.*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Beiboer et al., Guided selection of a pan carcinoma specific antibody reveals similar binding characteristics yet structural divergence between the original murine antibody and its human equivalent. J. Mol. Biol. 296: 833-849 (2000).*
Brown et al. Tolerance of single, but not multiple, amino acid replacements in antibody VH CDR 2: a means of minimizing B cell wastage from somatic hypermutation? J. Immuno. May 1996, 3285-91.*
Rudikoff et al Single amino acid substitution altering antigen-binding specificity. Proc Natl Acad Sci U S A. Mar. 1982;79(6):1979-83.*
Casset et al. A peptide mimetic of an anti-CD4 monoclonal antibody by rational design. Biochemical and Biophysical Research Communications, 307:198-205, 2003.*
Eduardo Padlan, Anatomy of the antibody molecule. Mol Immunol. Feb. 1994;31(3):169-217.*
Altschul et al., Basic local alignment search tool, J. Mol. Biol., 215(3):403-10 (1990).
Bird et al., Single-chain antigen-binding proteins, Science, 242(4877):423-6 (1988).
Devereux et al., A comprehensive set of sequence analysis programs for the VAX, Nucleic Acids Res., 12(1 Pt. 1):387-95 (1984).
Dolmans et al., Photodynamic therapy for cancer, Nat. Rev. Cancer, 3(5):380-7 (2003).
George et al., Isolating ligands specific for human vasculature using in vivo phage selection, Trends in Biotech., 21(5):199-203 (2003).
Hendrich et al., Experimental photodynamic laser therapy for rheumatoid arthritis with a second generation photosensitizer, Knee Surg. Sports Traumatol. Arthrosc., 8(3):190-4 (2000).
Holliger et al., "Diabodies": small bivalent and bispecific antibody fragments, Proc. Natl. Acad. Sci. USA, 90(14):6444-8 (1993).
Houdebine, Antibody manufacture in transgenic animals and comparisons with other systems, Curr. Opin. Biotechnol., 13(6):625-9 (2002).
Huang, A review of progress in clinical photodynamic therapy, Technol. Cancer Res. Treat., 4(3):283-93 (2005).
International Preliminary Report on Patentability for corresponding international application No. PCT/GB2011/051854, dated Apr. 2, 2013.

(Continued)

*Primary Examiner* — Maher Haddad
(74) *Attorney, Agent, or Firm* — Marshall, Gerstein & Borun LLP

(57) ABSTRACT

The present invention provides an antigen binding polypeptide which specifically targets the synovial microvasculature of arthritis patients and comprises one or more complementarity determining regions (CDRs) selected from the group consisting of SEQ ID NOs 1 to 4. The present invention also relates to the use of such antigen binding polypeptides and conjugates thereof for use in the diagnosis and treatment of arthritis.

18 Claims, 10 Drawing Sheets

(56) References Cited

OTHER PUBLICATIONS

International Search Report and Written Opinion for corresponding International Application No. PCT/GB2011/051854, mailing date Nov. 18, 2011.

Isaacs, Antibody engineering to develop new antirheumatic therapies, Arthritis Res. Ther., 11(3):225 (2009).

Kabat et al., Sequences of Proteins of Immunological Interest, 5th ed., U.S. Department of Health and Human Services, NIH Publication No. 91-3242 (1991).

Kamperidis et al., Development of a novel recombinant biotherapeutic with applications in targeted therapy of human arthritis, Arthritis & Rheumatism, 63(12):3758-67 (2011).

Kamperidis et al., Identification of single-chain antibody fragments specific for human synovial microvascular endothelium by in vivo phage display, Ann. Rheum. Dis., 66(Suppl 1):A12-A13 (2007).

Kipriyanov et al., Recombinant single-chain Fv fragments carrying C-terminal cysteine residues: production of bivalent and biotinylated miniantibodies, Mol. Immunol., 31(14):1047-58 (1994).

Kipriyanov et al., Single-chain antibody streptavidin fusions: tetrameric bifunctional scFv-complexes with biotin binding activity and enhanced affinity to antigen, Hum. Antibodies Hybridomas, 6(3):93-101 (1996).

Kremer et al., Rational use of new and existing disease-modifying agents in rheumatoid arthritis, Ann. Intern. Med., 134(8):695-706 (2001).

Lee et al., Identification of synovium-specific homing peptides by in vivo phage display selection, Arthritis Rheum., 46(8):2109-20 (2002).

Lewis et al., Identification of synovium-specific homing peptides by in vivo phage display selection, Arthritis & Rheumatism, 46(8):2109-20 (2002).

Muyldermans et al., Recognition of antigens by single-domain antibody fragments: the superfluous luxury of paired domains, Trends Biochem. Sci., 26(4):230-5 (2001).

Padlan et al., Identification of specificity-determining residues in antibodies, FASEB J., 9(1):133-9 (1995).

Petros et al., Strategies in the design of nanoparticles for therapeutic applications, Nat. Rev. Drug Discov., 9(8):615-27 (2010).

Potter et al., Antibody production in the baculovirus expression system, Int. Rev. Immunol., 10(2-3):103-12 (1993).

Qui et al., Small antibody mimetics comprising two complementarity-determining regions and a framework region for tumor targeting, Nat. Biotechnol., 25(8):921-9 (2007).

Schillberg et al., Molecular farming of recombinant antibodies in plants, Cell. Mol. Life Sci., 60(3):433-45 (2003).

Tatusova et al., BLAST 2 Sequences, a new tool for comparing protein and nucleotide sequences, FEMS Microbiol. Lett., 174(2):247-50 (1999).

Tatusova et al., Erratum to BLAST 2 Sequences, a new tool for comparing protein and nucleotide sequences, FEMS Microbiol. Lett., 177(1):187-8 (1999).

Taylor et al., Anti-TNF biologic agents: still the therapy of choice for rheumatoid arthritis, Nat. Rev. Rheumatol., 5(10):578-82 (2009).

Torchilin, Targeted pharmaceutical nanocarriers for cancer therapy and imaging, AAPS J., 9(2):E128-47 (2007).

Vigor et al., Nanoparticles functionalized with recombinant single chain Fv antibody fragments (scFv) for the magnetic resonance imaging of cancer cells, Biomaterials, 31(6):1307-15 (2010).

Wahid et al., Tumour necrosis factor-alpha (TNF-alpha) enhances lymphocyte migration into rheumatoid synovial tissue transplanted into severe combined immunodeficient (SCID) mice, Clin. Exp. Immunol., 122(1):133-42 (2000).

\* cited by examiner

| Heavy Chain | | Light Chain | |
|---|---|---|---|
| CDR2 | CDR3 | CDR2 | CDR3 |
| AIYTSGNSTSYADSVKG | NASNFDY | SASNLQS | QQGSDAPAT | variable amino acid domains are shown in bold

FIG. 6

ANTIBODY SPECIFICALLY BINDING SYNOVIAL MICROVASCULATURE OF ARTHRITIS PATIENTS

This application is the U.S. National Phase of International Application No. PCT/GB2011/051854, filed 30 Sep. 2011, incorporated herein by reference, which claims priority benefit of Great Britain patent application No. 1016494.5 filed 30 Sep. 2010.

FIELD OF THE INVENTION

The present invention relates to an antigen binding polypeptide which specifically targets the synovial microvasculature of arthritis patients. The polypeptide, and conjugates thereof, may be used in imaging the vasculature of joints and for the diagnosis and treatment of arthritis.

BACKGROUND TO THE INVENTION

Rheumatoid arthritis (RA) is one of the most common autoimmune diseases and a leading cause of chronic pain affecting over three million people in Europe alone. Rheumatoid arthritis affects 1 to 2% of the population. According to Medical Expenditure Panel Survey (MEPS) data, in the US the total costs incurred towards the treatment of rheumatoid arthritis and related arthritis in 2003 was $128 billion; the average per person cost is currently $8500. Each year, arthritis and its associated complications results in over 750,000 hospitalizations and 36 million outpatient visits. Up to 15% of people inflicted with any type of arthritis suffer from a reduction in the amount of physical activities they can perform. Typically when physical activity is reduced patients tend to develop depression because of their lack of independence and freedom.

In the UK there are around 400,000 adults with rheumatoid arthritis and arthritis is the most common condition for which people receive Disability Living Allowance. Over half a million people receive DLA as a result of arthritis (representing more than 18 percent of all DLA claimants), which is more than the total for heart disease, stroke, chest disease and cancer combined.

RA is an inflammatory disease of the synovial joints, which generally affects wrists, fingers, knees, feet, and ankles on both sides of the body. RA causes inflammation of the synovial membranes that line and protect the joints and tendons and, allow smooth and free movement of joints. Inflammation of the synovial membranes causes swelling of the affected joints and eventually leads to progressive cartilage destruction and erosion of bone, impairing range of movement and leading to deformity.

RA is an ongoing, progressive disease that also affects other organs of the body and can result in profound disability and life threatening complications. Hence, RA is a major cause of disability with a significant associated morbidity and mortality.

The onset age of RA is variable, ranging from children to individuals in their 90s. The prevalence of RA in populations of Western Europe and USA is approximately 1% with a female to male ratio of 3:1. Further, the total annual economic impact of rheumatoid arthritis is estimated at approximately £35 billion in Western Europe.

At a cellular level, the synovium is made up of a well organized matrix containing proteoglycan aggregates, a network of capillaries and lymphatic vessels and resident fibroblast and macrophage like cells. In RA, however, the synovium becomes infiltrated by T-helper cells, B cells, macrophages and plasma cells. Further, the synovium becomes hyperplastic and locally invasive at the interface between cartilage and bone causing destruction of articular cartilage, subchondral bone and periarticular soft tissue resulting in joint damage, deformity and profound disability in the long run (see FIG. 1).

It is now well established that angiogenesis (growth of new blood vessels from pre-existing vessels) in the synovium has a significant contribution to etiology and progression of this disease. Indeed, synovial angiogenesis may precede other pathological features of RA since synovial hypercellularity necessitates a compensatory increase in the number and density of synovial blood vessels.

The ultimate goals for the treatment of rheumatoid arthritis are to prevent joint damage, prevent loss of function and decrease the pain associated with RA. Non-steroidal anti-inflammatory drugs (NSAID) and disease modifying anti-rheumatic drugs (DMARD) are currently the major forms of treatment for RA, but they often come with significant side effects. NSAID can cause stomach irritation, gastrointestinal ulcers and kidney damage. The side effects of DMARDs depend on the type of drug used. Azathioprine increases the risk of infection, liver damage, hair loss and diarrhoea. Cyclosporine causes kidney damage, hypertension and enlarged gums. Chloroquine group causes gastritis, diarrhoea and vision problems. Gold salt can cause swelling of the tongue, bleeding gums, skin rash and kidney damage. Methotrexate can cause liver damage and bone marrow suppression. Sulfasalazine can cause gastrointestinal upset and allergic reactions. The newer biologic response modifiers depress the immune system and can cause reactivation of latent infections like tuberculosis.

Therapy for RA has been significantly improved in the last decade by the introduction of recombinant antibodies targeting a range of cytokines, T cells and B cells.

Since the initial approval of Etanercept, and shortly thereafter Infliximab, three additional TNF-neutralizing antibodies (Adalimumab, Certulizumab pegol and Golimumab) have been approved. Further, recombinant antibodies targeting T-cell [and/or dendritic cell], (Abatacept), B-cells, (Rituximab), and the receptor for cytokine IL-6, (Tocilizumab) have also been approved by the FDA for treatment of RA (Taylor and Feldmann 2009 Nat Rev Rheumatol 5(10): 578-582), (Isaacs 2009 Arthritis Res Ther 11(3): 225).

However, despite the obvious impact of the current therapies, prolonged treatment-free remission has not been obtained. Sustained and high magnitude clinical response is achieved by a minority (Taylor and Feldmann 2009, as above) and approximately 20-40% of patients do not respond to anticytokine therapy (Kremer 2001 Annals of Internal Medicine 134(8): 695-706). Also, the current therapeutics exhibit a number of associated adverse affects such as increased risks of infections and malignancies which make their persistent administration undesirable (Taylor and Feldmann 2009, as above).

Therefore, there is still a major unmet clinical need in RA and a requirement for alternative therapeutic options having a greater frequency of remission induction and improved safety profile with less systemic toxicity.

In the healthy joint (a) the thin synovial membrane lines the non-weight-bearing aspects of the joint. In rheumatoid arthritis (b) the synovial membrane becomes hyperplastic and infiltrated by chronic inflammatory cells. Ultimately it develops into 'pannus', which migrates onto and into the articular cartilage and underlying bone.

Figure 2:

FIG. 2—Immunohistological Analysis of In Vitro Reactivity of scFv A7 Antibody with Synovial Tissue Reactivity of scFv A7 with sections of synovial tissue was examined using biotinylated scFv A7.

Figure 3:
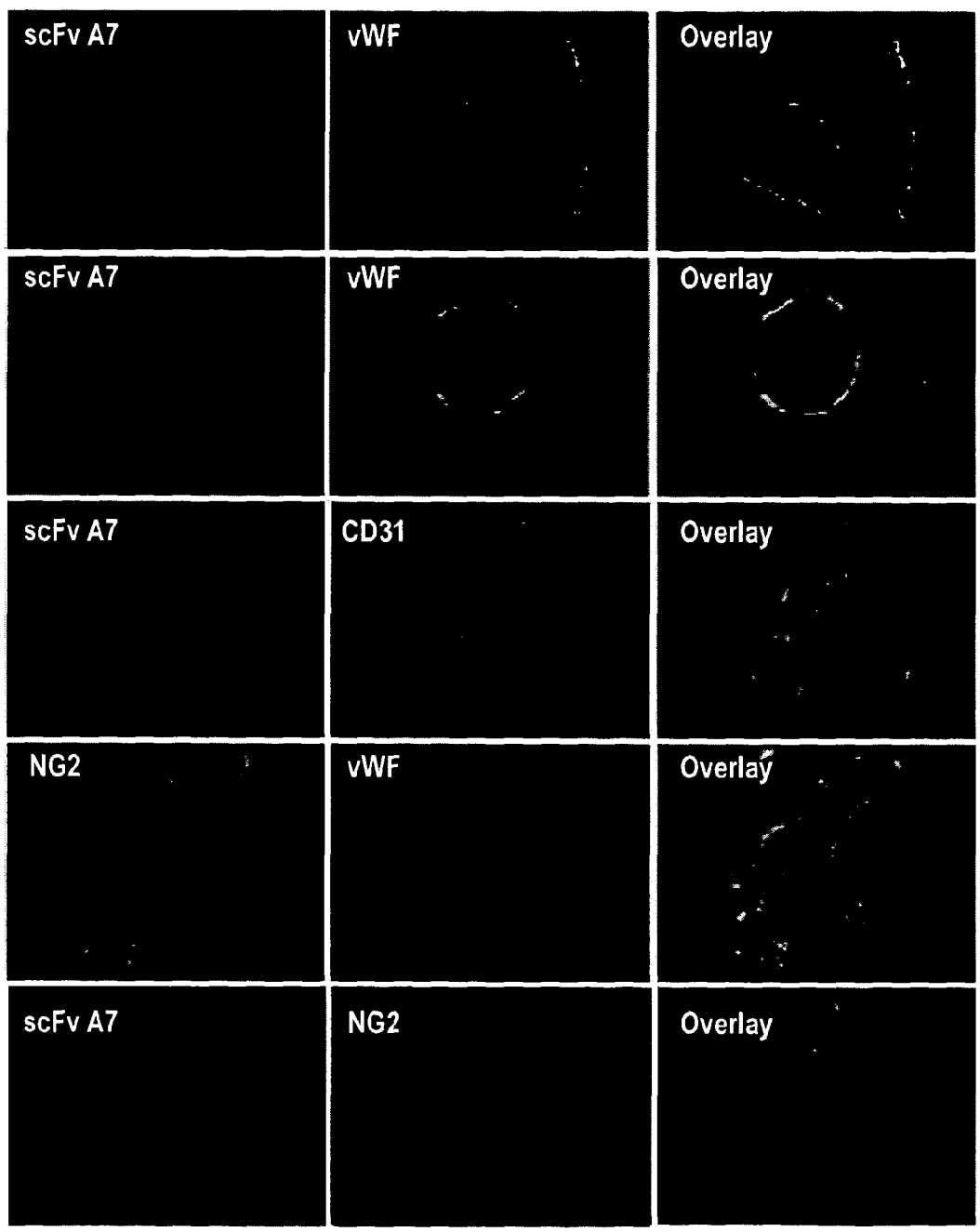

FIG. 3—Characterisation of Cellular Reactivity of scFv A7 within Synovial Microvasculature Reactivity of scFv with cellular components of synovial microvasculature was examined by dual staining of frozen human synovial tissue from RA patients with endothelial specific markers von Willerbrand factor (vWF) and CD 31 and the pericyte specific marker NG2. Bound scFv A7 was detected through its biotinylated tag using Texas Red—Avidin antibody. vWF, CD 31 and NG2 binding were detected by Alexa 488 (green) or Alexa 594 (red).

Figure 4:
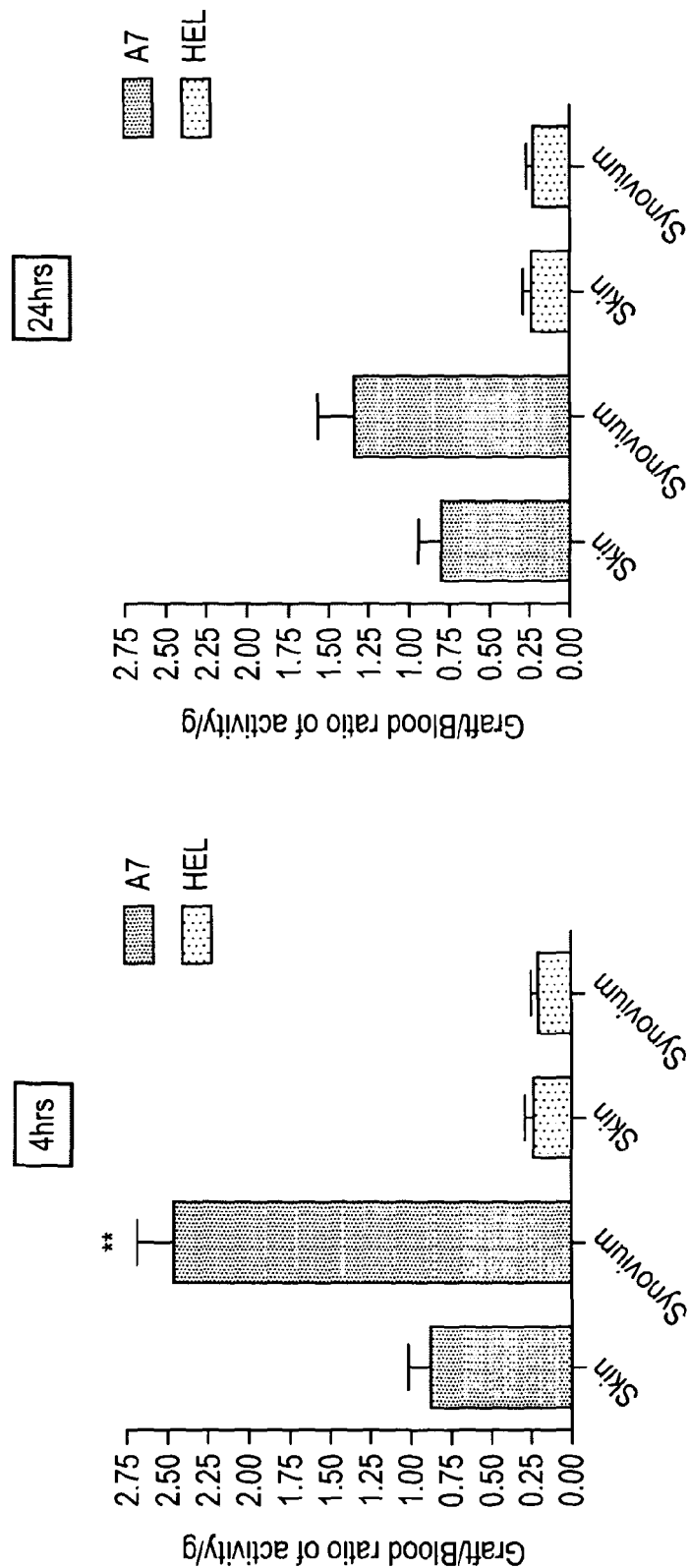

FIG. 4—In Vivo Targeting of Human Synovial Tissue with $I^{125}$ scFv A7

The ability of scFv to preferentialy target to microvasculature of synovial xenografts in vivo was examined by injecting iodinated scFv into SCID mice bearing dual synovial and skin xenografts. Graft tissue was examined 4 hours and 24 his post antibody administration by γ counting. The results were subsequently corrected for tissue weight and background radioactivity in the blood pool and expressed tissue to blood ratio of the percentage of the injected dose. N=5 for each condition. Iodinated scFv HEL was used as a negative control.

Figure 5:
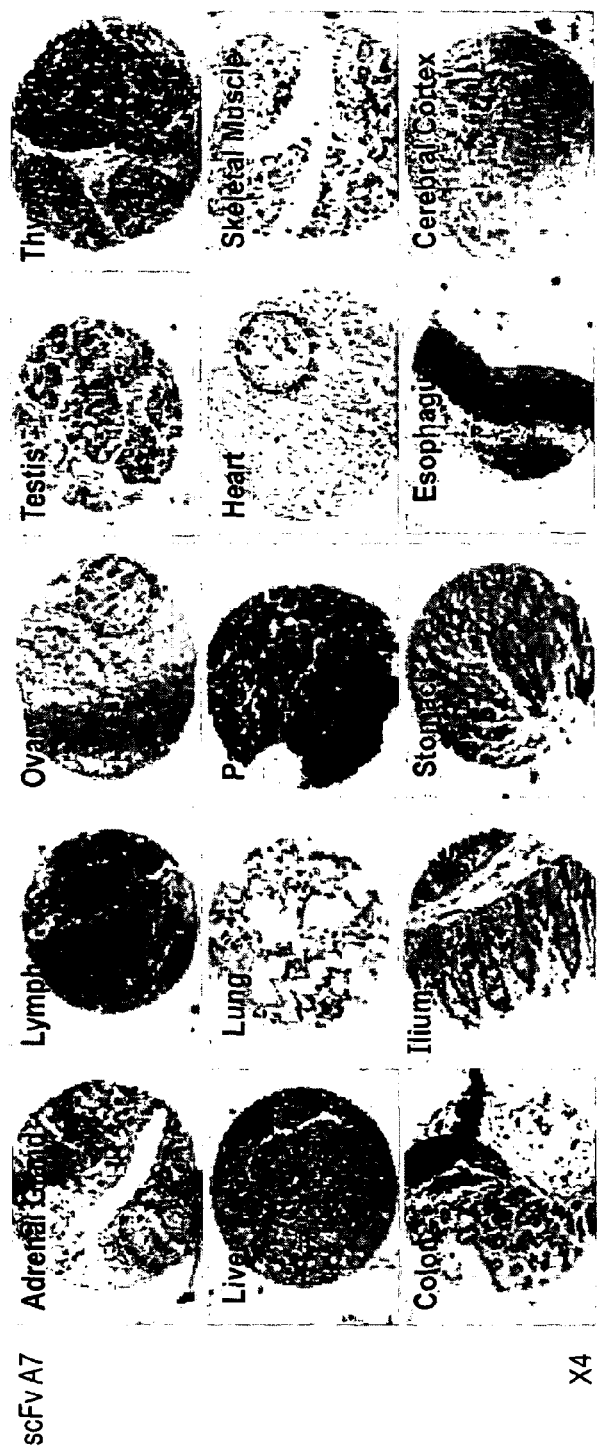
Figure 5:
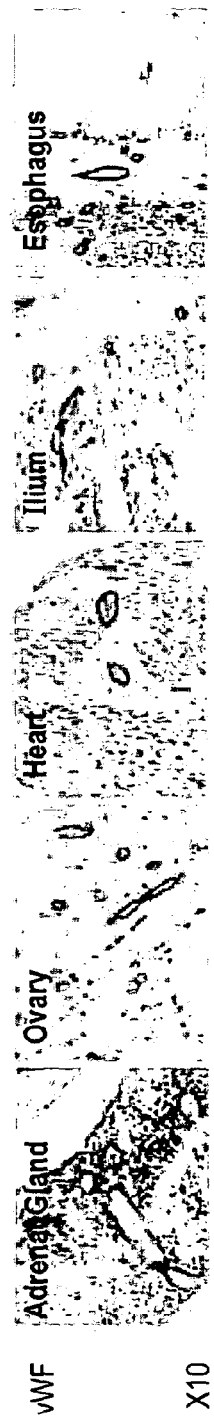

FIG. 5—Expression Profile of Reactivity of scFv Clones A7 with Normal Human Tissue as Assessed by Immunohistochemistry Reactivity of scFv A7 with normal human tissue was examined using paraffin embedded tissue microarrays of normal human tissue from various organs. Bound biotinylated scFv A7 antibody was detected through avidin HRP (brown). Anti von Willerbrand Factor was used to detect the presence of blood vessels in the tissue sections. Scale bar=20 um.

FIG. 6—CDR2 & CDR3 amino acid sequences of the heavy (SEQ ID NOs: 5-6) and light (SEQ ID NOs: 7-8) chains of scFv A7 Variable amino acid domains are shown. All antibody clones present in the library vary only in these positions and are otherwise identical.

Figure 7:
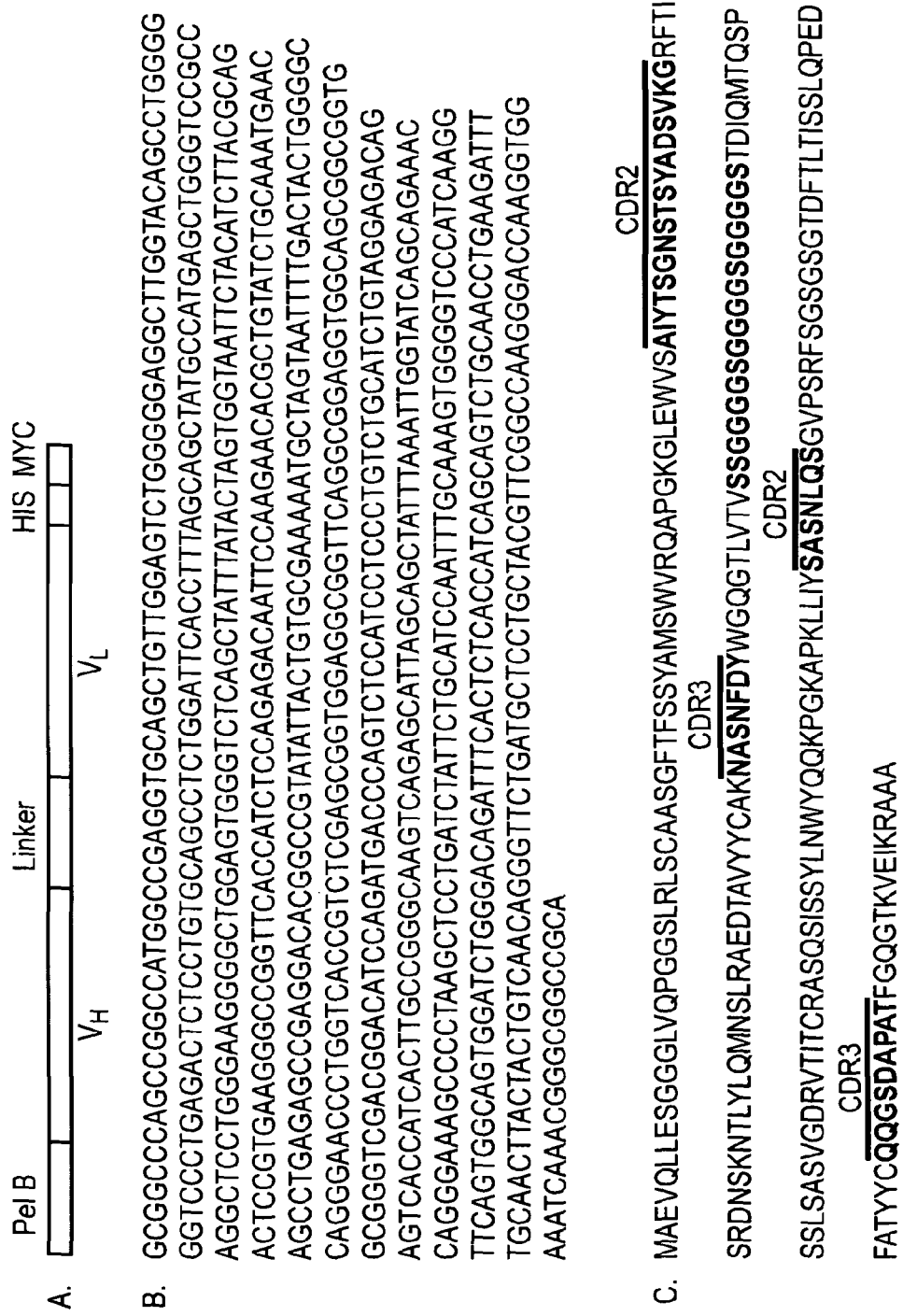

FIG. 7—Sequence of scFv A7

(A) Schematic diagram of scFv A7. (B) DNA sequence of scFv A7 (SEQ ID NO: 12). (C) Predicted amino acid sequence of scFv A7 (SEQ ID NO: 11). The peptide linker sequence (bold) and CDR region sequences (SEQ ID NOs: 5-8; bold, overlined, labeled) have been highlighted.

Figure 8:
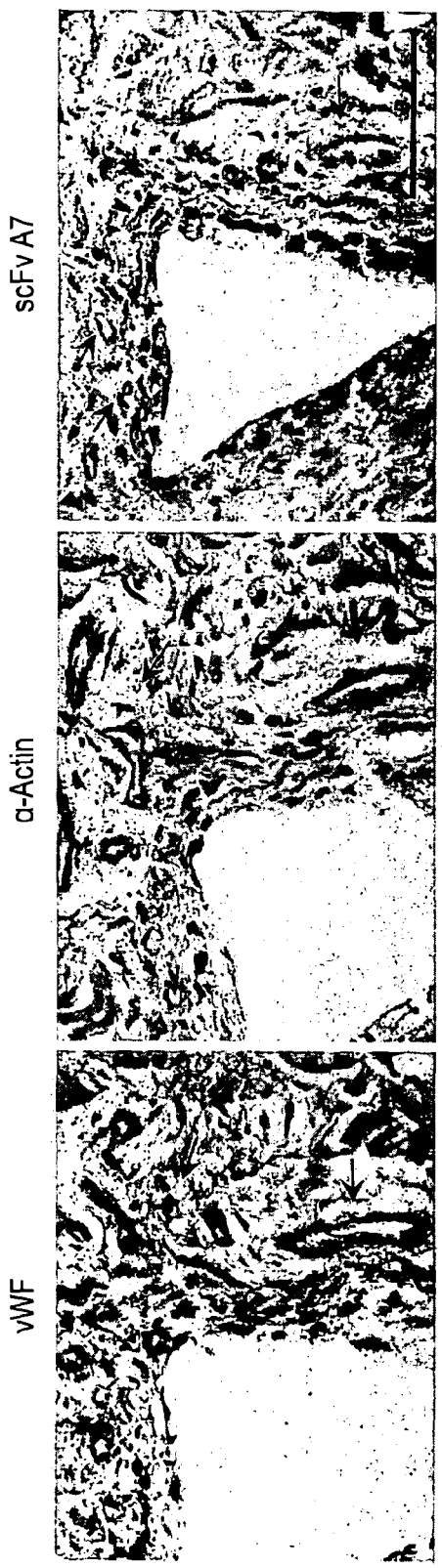

FIG. 8—Immunohistochemistry of scFv A7 in Normal Human Tissues

The reactivity of scFv A7 with normal human synovial tissue. Sequential sections show blood vessels that stain with vWF and α-actin. No reactivity is observed using scFv A7 antibody. The images shown are representative of the 11 independent samples examined. Scale bar=50 μm.

A: vWF
B: α-Actin
C: scFv A7

Figure 9:
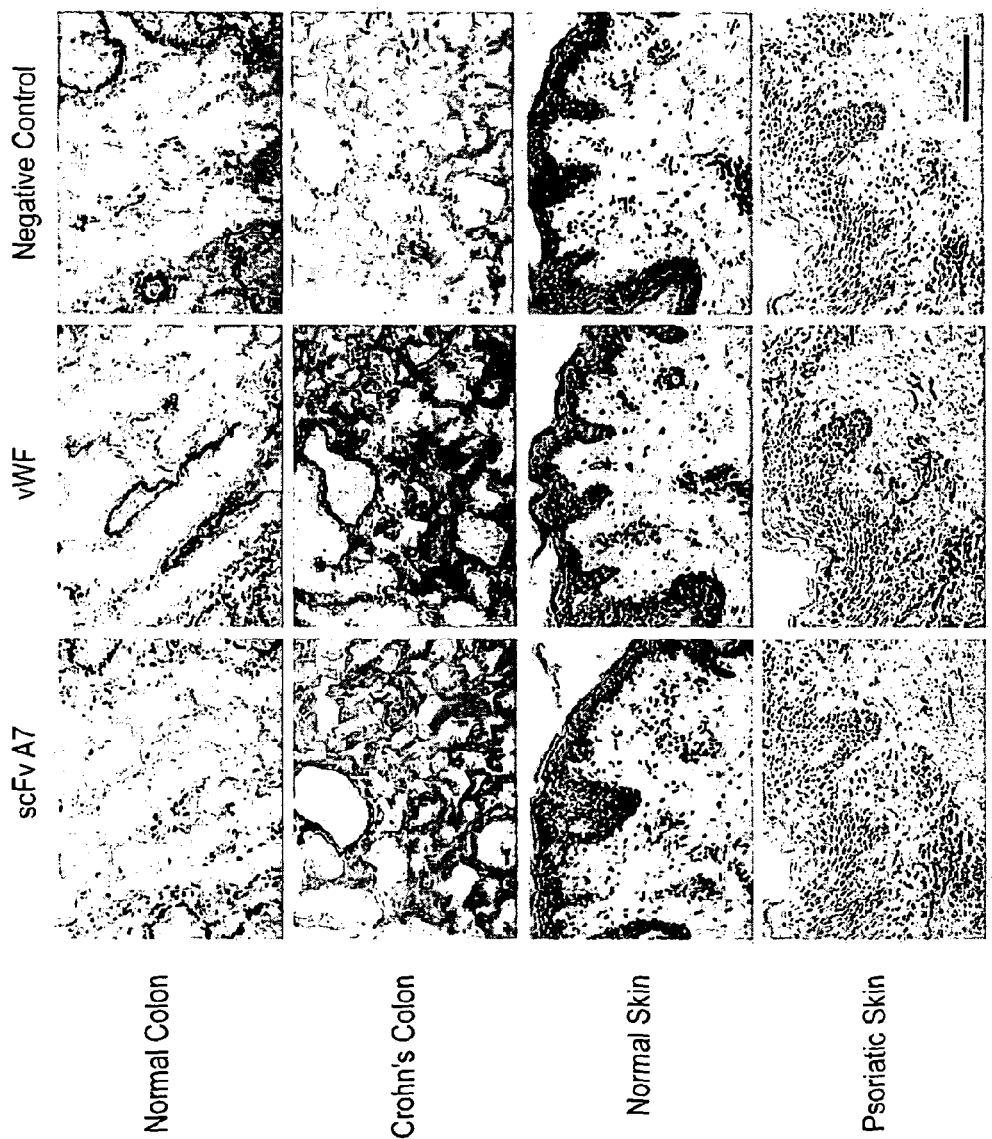

FIG. 9—Reactivity of scFv A7 Antibody with the Microvasculature of Inflammatory Tissues The reactivity of scFv A7 with normal colon, Crohn's colon, normal skin and psoriatic skin was assessed. The presence of microvasculature was visualised using anti-human vWF antibody. Biotinylated scFv A7 was detected with ABC-HRP. vWF antibody reactivity was detected using an HRP labeled secondary antibody. The images shown are representative of the 5 normal colon samples, 7 Crohn's colon samples and 5 skin samples examined. Scale bar=100 μm.

Figure 10:

FIG. 10—Reactivity of scFv A7 with PC3 Cells

Immunocytochemistry was used to examine the reactivity of scFv A7 with the cell surface of the prostate cancer cell line PC3. Reactivity with the cell surface was examined by using formaldehyde fixed but not permeablised cells. Bound scFv A7 was detected through its Myc tag by using anti c-Myc antibody followed by Alexa 488.

SUMMARY OF ASPECTS OF THE INVENTION

The present inventors have identified an scFv antibody which exhibits perivascular reactivity with the microvasculature of synovial tissue from RA patients, with little or no reactivity with normal tissue.

In a first aspect the present invention provides an antigen binding polypeptide which specifically targets the synovial microvasculature of arthritis patients and comprises one or more complementarity determining regions (CDRs) selected from the group consisting of SEQ ID NOs 1 to 4.

The antigen binding polypeptide may comprise one or more complementarity determining regions (CDRs) selected from the group consisting of SEQ ID NOs 5 to 8.

The antigen binding polypeptide may react with the stromal compartment of the microvasculature and/or with pericytes and may exhibit perivascular reactivity.

The antigen binding polypeptide may comprise a VH sequence as shown in SEQ ID NO: 9 and/or a VL sequence as shown in SEQ ID NO: 10.

The antigen binding polypeptide may be an scFv.

The antigen binding polypeptide may be fully human.

The antigen binding polypeptide may specifically target the synovial microvasculature of osteoarthritis and/or rheumatoid arthritis patients.

The present invention also provides an antigen binding polypeptide which binds to the same epitope as an antigen binding polypeptide according to the first aspect of the invention. The antigen binding polypeptide may bind to the same epitope as an antigen binding polypeptide comprising the amino acid sequence shown as SEQ ID No 11.

The present invention also provides an antigen binding polypeptide which is associated with another agent. The antigen-binding polypeptide may, for example, be conjugated to the other agent. The agent may comprise one or more of the following: a therapeutic cytokine, an anti-angiogenic agent, an anti-rheumatic drug; a photosensitive agent or a magnetic nanoparticle.

The present invention also provides an antigen binding polypeptide according to the first aspect of the invention or a conjugate thereof: for use in the treatment of RA; for use in imaging the vasculature of joints and/or for use in the diagnosis, monitoring or prognosis of arthritis.

In a second aspect, the present invention provides a method for treating arthritis in a subject, which comprises the step of administering an antigen binding polypeptide according to the first aspect of the invention or a conjugate thereof to a subject.

The method may comprise the following steps:
(i) administration of an antigen binding polypeptide according to the first aspect of the invention, conjugated to a photosensitive agent, to a subject;
(ii) targeting the conjugate to the synovial vasculature of a joint;
(ii) application of light to the joint in order to activate the photosensitive agent within the synovial vasculature.

The method may comprise the following steps:
(i) administration of an antigen binding polypeptide according to the first aspect of the invention, conjugated to a magnetic nano particles, to a subject;
(ii) targeting the conjugate to the synovial vasculature of a joint;
(ii) application of a magnetic field to the joint in order to activate the magnetic nano particles within the synovial vasculature.

In such methods, activation of the agent may lead to disruption of existing vasculature.

The method may be a combination method, involving the simultaneous, separate or sequential use of another therapeutic. For example, treatment may also involve administration of TNF-α blockade therapeutics.

The method may be for treating osteoarthritis and/or rheumatoid arthritis.

In a third aspect the present invention provides a method for targeting an agent to the synovial microvasculature which comprises the step of forming an association between the agent with an antigen binding polypeptide of the first aspect of the invention in vitro. The agent may, for example, be conjugated to the antigen-binding polypeptide. The association may be such that, when the agent/antigen-binding polypeptide is administered to an arthritis patient, the agent accumulates selectively in neo-vascular sites.

The agent may be a therapeutic, imaging or diagnostic agent. For example, the agent may be a therapeutic cytokine, an anti-angiogenic agent, anti-rheumatic drug, a photosensitive agent or a magnetic nanoparticle.

In a fourth aspect the present invention provides a nucleic acid sequence encoding an antigen binding polypeptide according to the first aspect of the invention or a conjugate thereof.

The nucleic acid sequence may comprise the sequence shown as SEQ ID No 12 or a variant thereof.

In a fifth aspect, the present invention provides a vector comprising a nucleic acid sequence according to the fourth aspect of the invention.

In a sixth aspect, the present invention provides a host cell comprising a nucleic acid according to the fourth aspect of the invention or a vector according to the sixth aspect of the invention.

The antigen binding polypeptide of the present invention represents a unique tool, which serves as a versatile vascular targeting agent which may, for example, be used in selective biopharmaceuticals for the treatment of rheumatoid disease.

The antigen binding polypeptide of the present invention addresses many of the problems associated with existing recombinant antibody therapies for the treatment of arthritis. For example, due to the fact the polypeptide exhibits perivascular reactivity within the synovial tissue with no significant reactivity with normal tissue, it may be used to deliver a higher concentration of conventional or biologic drugs to the site of disease.

DETAILED DESCRIPTION

Antigen Binding Polypeptide

The first aspect of the invention relates to an antigen binding polypeptide.

The term "antigen-binding polypeptide" is used to mean a polypeptide which comprises one or more complementarity determining regions (CDRs) and binds antigen in the same way as antibody or antibody-like molecule.

A classical antibody molecule comprises four polypeptide chains: two heavy (H) chains; and two light (L) chains interconnected by disulfide bonds. Each heavy chain is comprised of a heavy chain variable region (VH) and a heavy chain constant region. The heavy chain constant region is comprised of three domains, CH1, CH2 and CH3. Each light chain is comprised of a light chain variable region (VL) and a light chain constant region. The light chain constant region is comprised of one domain, CL. The VH and VL regions can be further subdivided into regions of hypervariability, termed complementarity determining regions (CDRs)1 interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

In a classical antibody molecule, the pairing of heavy and light chains brings together the CDRs from each chain to create a single hypervariable surface which forms the antigen-binding site at the tip of each of the Fab arms. It is common for only a subset of the six total CDRs to contribute to antigen binding. For example when the antibody MOPC 603 binds to phosphochlorine the light-chain variable region contributes only CDR3 to the binding site, whereas all three CDRs from the heavy chain are involved.

The antigen-binding polypeptide may comprise 2, 3, or 4 CDRs from the group shown as SEQ ID No 1-4.

It is also possible for a single VH or VL chain to bind antigen, for example in domain antibodies (dAbs—see below). The antigen-binding polypeptide may comprise both VH CDRs (SEQ ID Nos 1 and 2) and/or both VL CDRs (SEQ ID Nos 3 and 4).

The term "antibody" includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced IL 13 binding and/or reduced FcR binding).

The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Binding fragments include Fab, Fab', F(ab')2, Fabc, Fd, dAb, Fv, single chains, single-chain antibodies, e.g., scFv, single domain antibodies (Muldermans et al., 2001 J. Biotechnol. 26:230-5), and an isolated complementarity determining region (CDR).

A Fab fragment is a monovalent fragment consisting of the VL, VH, CL and CH1 domains. A F(ab')2 fragment is a bivalent fragment comprising two Fab fragments linked by a disulfide bridge at the hinge region. An Fd fragment consists of the VH and CH 1 domains, and an Fv fragment consists of the VL and VH domains of a single arm of an antibody.

A dAb fragment consists of a single VH domain or VL domain which alone is capable of binding an antibody (WO 90/05144; WO 03/002609). Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, et al., 1993, Proc. Natl. Acad. Sci. USA 90:6444-6448).

The antigen-binding polypeptide described in the Examples is an scFv fragment. In a classical antibody molecule, the two domains of the Fv fragment, VL and VH, are coded for by separate genes. However they can be joined, using recombinant methods, by a synthetic linker that enables them to be made as a single protein chain known as single chain Fv (scFv) in which the VL and VH regions pair to form monovalent molecules (Bird et al., 1988, Science 242:423-426).

Antibody-like molecules include the use of CDRs separately or in combination in synthetic molecules such as SMIPs and small antibody mimetics. Specificity determining regions (SDRs) are residues within CDRs that directly interact with antigen. The SDRs correspond to hypervariable residues. See (Padlan et al. (1995) FASEB J. 9: 133-139). CDRs can also be utilized in small antibody mimetics, which comprise two CDR regions and a framework region (Qui et al. Nature Biotechnology Vol 25; 921-929; August 2007).

An antibody or binding portion thereof also may be part of a larger immunoadhesion molecules formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

The antigen-binding polypeptide of the present invention comprises one or more complementarity determining region(s) (CDR(s)) selected from the group consisting of SEQ ID NO: 1 to 4.

CDRs

```
SEQ ID NO: 1:
AXYTSXNSXSXXXXXXX

SEQ ID NO: 2:
NASNXXX

SEQ ID NO: 3:
SXXNXXX

SEQ ID NO: 4:
XXGSDAXAX
```

X can be any amino acid.

For a given CDR, one or more of the amino acids represented by X in SEQ ID NOs: 1-4 may be as shown in SEQ ID NOs: 5-8.

```
SEQ ID NO: 5:
AIYTSGNSTSYADSVKG

SEQ ID NO: 6:
NASNFDY

SEQ ID NO: 7:
SASNLQS

SEQ ID NO: 8:
QQGSDAPAT
```

For example, a CDR according to SEQ ID NO: 1 may be one of the following:

```
SEQ ID NO: 15:
AIYTSXNSXSXXXXXXX;

SEQ ID NO: 16:
AXYTSGNSXSXXXXXXX;

SEQ ID NO: 17:
AXYTSXNSTSXXXXXXX;

SEQ ID NO: 18:
AXYTSXNSXSYXXXXXX;

SEQ ID NO: 19:
AXYTSXNSXSXAXXXXX;

SEQ ID NO: 20:
AXYTSXNSXSXXDXXXX;

SEQ ID NO: 21:
AXYTSXNSXSXXXSXXX;

SEQ ID NO: 22:
AXYTSXNSXSXXXXVXX;

SEQ ID NO: 23:
AXYTSXNSXSXXXXXKX;
or

SEQ ID NO: 24:
AXYTSXNSXSXXXXXXG.
```

For a given CDR, two, three, four, five or more of the amino acids represented by X may be as shown in SEQ ID NOs: 5-8.

The antigen-binding polypeptide of the invention may comprise at least one CDR selected from the group consisting of SEQ ID NOs: 5-8.

V Regions

The antigen-binding polypeptide of the invention may comprise a CDR selected from the group consisting of SEQ ID Nos 1, 2, 5 and 6 as part of a VH region.

The antigen-binding polypeptide of the invention may comprise a CDR selected from the group consisting of SEQ ID Nos 3, 4, 7 and 8 as part of a VL region.

The antigen-binding polypeptide of the invention may comprise a CDR selected from the group consisting of SEQ ID Nos 1, 2, 5 and 6 as part of a VH region; and a CDR selected from the group consisting of SEQ ID Nos 3, 4, 7 and 8 as part of a VL region.

The antigen-binding polypeptide of the invention may comprise two CDRs corresponding to SEQ ID Nos 1 and 2 (or 5 and 6) as part of a VH region.

The antigen-binding polypeptide of the invention may comprise two CDRs corresponding to SEQ ID Nos 3 and 4 (or 7 and 8) as part of a VL region.

The antigen-binding polypeptide of the invention may comprise two CDRs corresponding to SEQ ID NOs: 1 and 2 (or 5 and 6) as part of a VH region; and two CDRs corresponding to SEQ ID NOs: 3 and 4 (or 7 and 8) as part of a VL region.

The antigen binding polypeptide may comprise a VH region as shown in SEQ ID NO: 9 or a variant thereof having, for example, at least 70, 80, 90, 95 or 99% sequence identity.

```
SEQ ID NO: 9:
MAEVQLLESGGGLVQPGGSLRLSCAASGFTFSSYAMSWVRQAPGKGLEWV

SAIYTSGNSTSYADSVKGRFTISRDNSKNTLYLQMNSLRAEDTAVYYCAK

NASNFDYWGQGTLVTV
```

The antigen binding polypeptide may comprise a VL region as shown in SEQ ID NO: or a variant thereof having, for example, at least 70, 80, 90, 95 or 99% sequence identity.

SEQ ID NO: 10:
TDIQMTQSPSSLSASVGDRVTITCRASQSISSYLNWYQQKPGKAPKLLIY

SASNLQSGVPSRFSGSGSGTDFTLTISSLQPEDFATYYCQQGSDAPATFG

QGTKVEIKRAAA

For both the VH and VL regions, variations in the sequence may be concentrated in the framework regions of the polypeptide (i.e. those portions shown in black on FIG. 7B). The CDRs (corresponding to the portions shown in brown) may comprise relatively few amino acid substitutions. The CDRs should only comprise substitutions in the positions corresponding to those shown in red in FIG. 6, i.e. those represented by amino acid X in SEQ ID No 1-4 and not the other CDR positions (those shown in black in FIG. 6).

SCFV

The antigen binding polypeptide may be an scFv having the sequence shown as SEQ ID No 11 or a variant thereof having, for example, at least 70, 80, 90, 95 or 99% sequence identity.

SEQ ID No 11:
MAEVQLLESGGGLVQPGGSLRLSCAASGFTFSSYAMSWVRQAPGKGLEWV

SAIYTSGNSTSYADSVKGRFT1SRDNSKNTLYLQMNSLRAEDTAVYYCAK

NASNFDYWGQGTLVTVSSGGGGSGGGGSGGGGSTDIQMTQSPSSLSASVG

DRVTITCRASQSISSYLNWYQQKPGKAPKLLIYSASNLQSGVPSRFSGSG

SGTDFTLTISSLQPEDFATYYCQQGSDAPATFGQGTKVEIKRAAA

Again, variations in the sequence may be concentrated in the framework regions and linker region of the polypeptide (i.e. those portions shown in black and red respectively on FIG. 7B). The CDRs (corresponding to the portions shown in brown) may comprise relatively few amino acid substitutions. The CDRs may only comprise substitutions in the positions corresponding to those shown in red in FIG. 6, i.e. those represented by amino acid X in SEQ ID No 1-4.

Sequence Comparisons

Identity comparisons can be conducted by eye, or more usually, with the aid of readily available sequence comparison programs. These commercially available computer programs can calculate % identity between two or more sequences. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbial Lett 1999 177(1): 187-8 and tatiana@ncbi.nlm.nih.gov).

The sequence may have one or more deletions, insertions or substitutions of amino acid residues which produce a silent change and result in a functionally equivalent molecule. Deliberate amino acid substitutions may be made on the basis of similarity in polarity, charge, solubility, hydrophobicity, hydrophilicity, and/or the amphipathic nature of the residues as long as the activity is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Human Antibody

The antigen binding polypeptide may be non-human, chimaeric, humanised or fully human.

Non-human antibodies include polyclonal or monoclonal antibody preparations from mouse, rat, rabbit, sheep, goat or other mammals.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. A crude polyclonal antibody preparation may be obtained by immunising an animal with antigen.

Chimeric antibodies comprise sequences from at least two different species. As one example, recombinant cloning techniques may be used to include variable regions, which contain the antigen-binding sites, from a non-human antibody (i.e., an antibody prepared in a non-human species immunized with the antigen) and constant regions derived from a human immunoglobulin.

The antigen binding polypeptide may be humanized.

"Humanized" forms of non-human (e.g., murine) antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also may comprise at least a portion of an immunoglobulin constant region (Fc), typically that of a human immunoglobulin.

The antigen binding polypeptide may be fully human, as is the case for the scFv described in the Examples.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. The mutations may be introduced, for example, using a selective mutagenesis approach. A human antibody may have at least one position replaced with an amino acid residue, e.g., an activity enhancing amino acid residue, which is not encoded by the human germline immunoglobulin sequence. A human antibody may have some amino acid changes within the CDR regions. However, the term "human antibody" as used herein is not intended to include antibodies in which CDR sequences derived from the germline of another mammalian species, such as a mouse, have been grafted onto human framework sequences.

Fully human recombinant antibodies are likely to be considerably less immunogenic than non-human (e.g. murine), chimeric or humanised antibodies when used for therapy as they comprise effectively no foreign sequence.

Reactivity

The antigen binding polypeptide of the present invention specifically targets the microvasculature of arthritis patients. For example, the antigen binding polypeptide may target the microvasculature of osteoarthritis or rheumatoid arthritis (RA) patients.

Figure 1:
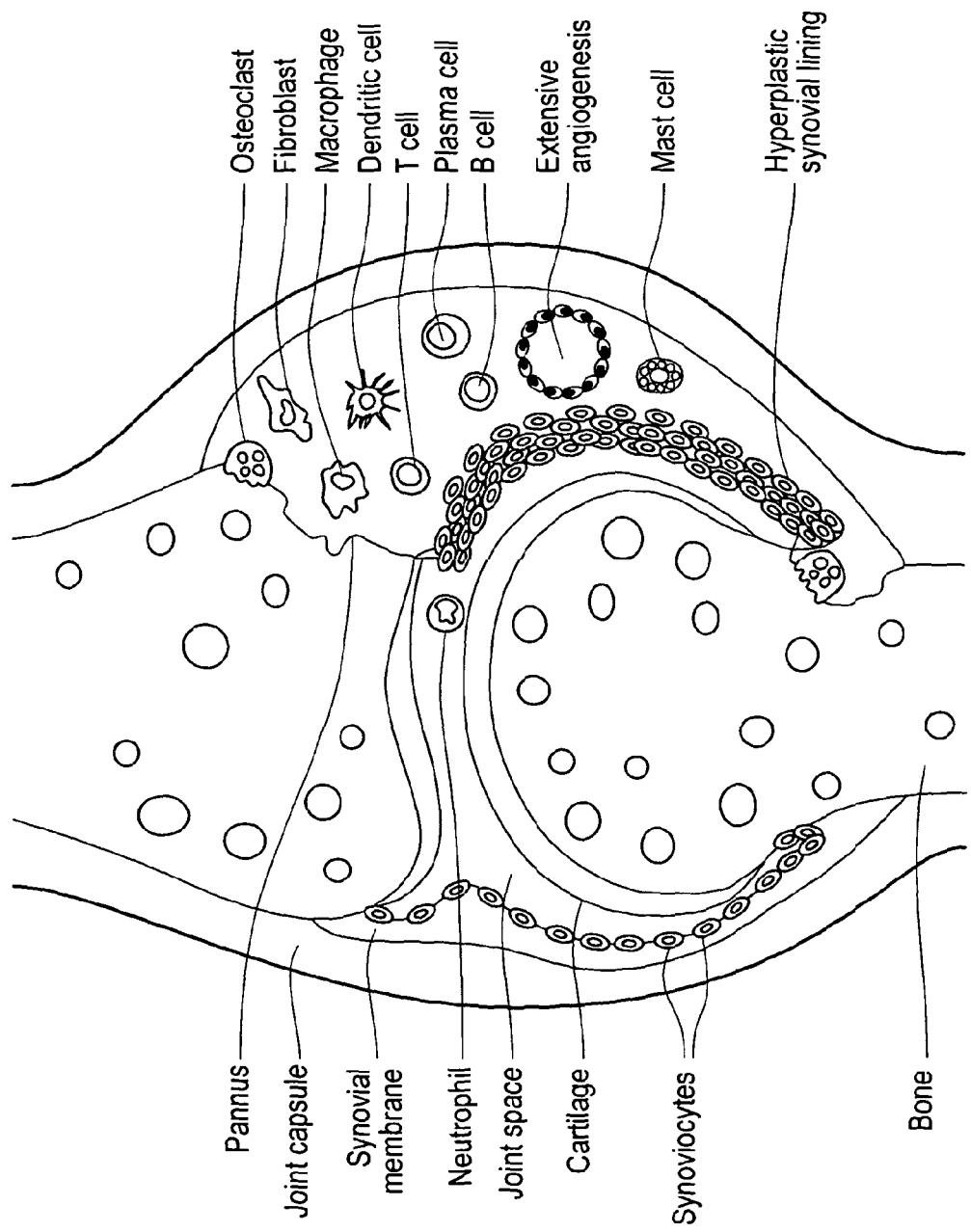
FIG. 1—Comparison of a Normal Joint and a Rheumatoid Arthritis Joint

As shown in FIG. 1, in a normal joint, the synovial membrane lines the non-weight bearing aspects of the joint. In arthritis, the synovium becomes infiltrated by T-helper cells, B cells, macrophages and plasma cells. Extensive angiogenesis occurs in the synovium, significantly increasing the microvasculature. The antigen binding polypeptide of the present invention exhibits specific reactivity with this synovial microvasculature.

The antigen binding polypeptide may react with the stromal (i.e. connective tissue) compartment of the microvasculature. The stromal compartment of the microvasculature is attractive for antibody-based targeting applications, since the compartment is stable and present in abundance.

The antigen binding polypeptide may react with pericytes. Pericytes, also known as Rouget cells or mural cells, are associated abluminally with all vascular capillaries and post-capillary venules. Pericyte specificity may be investigated by dual staining with a pericyte-specific marker such as NG2, as described in the Examples.

The antigen-binding polypeptide may bind the cell surface of the smooth muscle cells found in the synovial microvasculature.

The antigen binding polypeptide may exhibit perivascular reactivity, i.e. it may preferentially bind to sites around the blood vessels within the synovial microvasculature.

The antigen-binding polypeptide of the present invention "specifically targets" the synovial vasculature of arthritis patients in the sense that, following administration to a patient, the antigen-binding polypeptide exhibits a preferential binding capacity to synovium as opposed to other tissue (e.g. skin). The antigen-binding polypeptide may exhibit a two-three- or four-fold preferential binding capacity for arthritic synovium to other tissues.

The antibody binding polypeptide of the present invention should not exhibit significant reactivity with vital organs, such as heart, liver, lung, pancreas, cerebral cortex and digestive system.

The antibody binding polypeptide of the present invention should not exhibit significant reactivity with normal tissue such as lymph, thymus, adrenal gland, ovary and testis.

The antibody binding polypeptide of the present invention should not significantly target normal, non-arthritic joints. For example, when administered to an arthritis patient who has a combination of arthritic and normal joints, the antibody-binding polypeptide should preferentially target to the arthritic joints. The antibody-binding polypeptide may preferentially target and/or accumulate at joints showing the highest amount of synovial angiogenesis.

Reactivity and/or targeting is considered "significant" if it renders a diagnostic product based on the antibody-binding polypeptide unsuitable for use due to high background levels, or renders a therapeutic product based on the antigen-binding polypeptide unsafe or ineffective for use due to low levels of specificity.

Complex/Conjugate

The antigen binding polypeptide may be associated with another agent for use in the diagnosis and/or treatment of rheumatoid disease or imaging the vasculature of joints.

The association is such that, when the antigen-binding polypeptide/agent complex is administered to an arthritic subject, the agent is targeted to the synovial microvasculature by virtue of its association with the antigen-binding polypeptide.

The agent may be part of or in a nanocarrier, such as a nanoparticle or liposome. The nanocarrier may be associated with, for example coated with the antigen-binding polypeptide (Petros and DeSimone 2010 Nature Reviews Drug Discovery 9, p 615-627; Torchilin The AAPS Journal 2007; 9 (2) p 129-1470).

Alternatively, the antigen-binding polypeptide may be conjugated to the agent(s). Techniques for conjugation of proteins are known in the art. For example, the antigen-binding polypeptide and agent may be linked via a linker, generally a flexible linker (such as a polypeptide chain) or a chemical linking group.

The antigen-binding polypeptide and the agent may be encoded by a single nucleic acid sequence and expressed together as a fusion protein. Alternatively the antigen-binding polypeptide and the agent or may be separately expressed and subsequently linked together, for example using chemical linking agents.

Where the agent is itself an antibody or part thereof, the antigen binding polypeptide of the invention and the agent may be associated as a dual-specific ligand, such as a bifunctional antibody. The agent may, for example, be based on an antibody currently used for the treatment of RA such as Adalimumab, Certulizumab pegol, Golimumab, Abatacept, Rituximab or Tocilizumab.

The agent may be one or more of the following: a therapeutic cytokine, an anti-angiogenic agent, an anti-rheumatic drug; a photosensitive agent or a magnetic nanoparticle.

The agent may be capable of blocking one or more cytokines. For example, the agent may be capable of blocking TNFα, IL-1, IL-6, IL-15, IL-12/23, IL-17, IL-18, IL-27, or IL-32.

The agent may interact with the cytokine directly or its receptor (for example by being a cytokine receptor antagonist).

Anti-angiogenic agents work to block blood vessel growth in one of three ways: (i) blocking the growth factor from reaching the cell; (ii) blocking signaling within the cell; (iii) interfering with signaling between cells.

Vascular endothelial growth factor (VEGF) is responsible for the growth of new blood vessels. It promotes this growth by stimulating the endothelial cells, which form the walls of the vessels and transport nutrients and oxygen to the tissues. Blocking VEGF, thus inhibits the growth of new blood vessels from growing.

Bevacizumab (Avastin) is a clinically approved monoclonal antibody therapeutic which blocks VEGF.

Other treatments block intracellular signalling within endothelial cells which would otherwise lead to angiogenesis. One such type of drug is tyrosine kinase inhibitors (TKIs) such as Sunitinib (Sutent).

Another treatment that affects the formation of blood vessels is thalidomide, which interferes with cell signalling. Lenalidomide (Revlimid) is a thalidomide drug developed to have fewer side affects.

The major classes of antirheumatic drugs include: Nonsteroidal Anti-Inflammatory Drugs (NSAIDs); corticosteroids; Disease Modifying Anti-Rheumatic Drugs (DMARDs); Slow-Acting Antirheumatic Drugs (SAARDs); and Immunosuppresive cytotoxic drugs.

Nonsteroidal Anti-Inflammatory Drugs (NSAIDs) bring symptomatic relief of both inflammation and pain, but have a limited effect on the progressive bone and cartilage loss associated with rheumatoid arthritis. They act by slowing the body's production of prostaglandins. Common NSAIDs include: ibuprofen (Motrin, Nuprin or Advil), naproxen (Naprosyn, Aleve) and indomethacin (Indocin).

Corticosteroids are very powerful antiinflammatory agents. They are the synthetic analogs of cortisone, produced by the body. Corticosteroids are used to reduce inflammation and suppress activity of the immune system. The most commonly prescribed are prednisone and dexamethasone.

Disease Modifying Anti-Rheumatic Drugs (DMARDs) influence the disease process itself rather than only treating symptoms. DMARDs also have anti-inflammatory effects, and most were derived from the treatment of other diseases, such as cancer and malaria. Antimalarials DMARDs include chloroquine (Aralen) and hydroxychloroquine (Plaquenil). Powerful DMARDs include: methotrexate (Rheumatrex), sulfasalazine, cyclosporine, azathioprine (Imuran) and cyclophosphamide (Cytoxan), azathioprine, sulfasalazine, penicillamine, and organic gold compounds such as aurothioglucose (Solganol), gold sodium thiomalate (Aurolate) and auranofin (Ridaura).

Slow-Acting Antirheumatic Drugs (SAARDs) are a special class of DMARDs and the effect of these drugs is slow acting and not so quickly apparent as that of the NSAIDs. Examples are hydroxychloroquine and aurothioglucose.

Immunosuppresive cytotoxic drugs may be used if treatment with NSAIDs and SAARDs has had no effect. Immunosuppresive drugs have a stabilizing effect on the immune system. Since the inflammation associated with chronic arthritis is due to malfunctions of the immune system, use of this class of drugs has been shown to be beneficial for the treatment of rheumatoid arthritis as well. Examples are: methotrexate, mechlorethamine, cyclophosphamide, chlorambucil, and azathioprine.

The agent may be an enzyme, such as a pro-drug activating enzyme.

A photosensitive agent is one which, when present in the synovium and activated by light causes disruption of the existing vasculature. Examples of such agent are known in the art, such as those described in Dolmans et al Nature Reviews Cancer 2003, 3, 380-387; Huang, Technol Cancer Res Treat. 2005, 4(3): 283-293; Hendrich et al Knee Surg, Sports Traumatol, Arthrosc (2000) 8:190-194.

Photosensitizers are molecules that, on irradiation and in the presence of oxygen, release toxic diffusible agents such as singlet oxygen or reactive radicals. The anti-ED-B antibody fragment scFv(L19) selectively localizes to newly formed blood vessels in a rabbit model of ocular angiogenesis. When chemically coupled to a photosensitizer and irradiated with red light, this immunoconjugate mediates the complete and selective occlusion of ocular neovasculature and promotes apoptosis of the corresponding endothelial cells. Photosensitizers are already used in the clinic for the photodynamic therapy of certain forms of age-related macular degeneration.

The agent may be or comprise a magnetic nanoparticle. When activated by a magnetic field, the agent may be able to cause disruption of the existing synovial microvasculature.

Suitable magnetic nanoparticles are known in the art, such as those described in Vigor et al Biomaterials. 2010 February; 31(6):1307-15.

The present invention also provides a complex, such as a conjugate, comprising an antigen-binding polypeptide according to the first aspect of the invention and an agent.

The complex may be for therapeutic and/or diagnostic use.

Nucleic Acid Sequence

The present invention also provides a nucleotide sequence capable of encoding an antigen binding polypeptide according to the present invention or conjugate thereof.

The nucleic acid sequence may comprise all or part of the sequence shown as SEQ ID No 12 or a variant thereof having at least 70, 80, 90, 95 or 99% sequence identity.

SEQ ID No. 12
GCGGCCCAGCCGGCCATGGCCGAGGTGCAGCTGTTGGAGTCTGGGGGAG

GCTTGGTACAGCCTGGGGGGTCCCTGAGACTCTCCTGTGCAGCCTCTGG

ATTCACCTTTAGCAGCTATGCCATGAGCTGGGTCCGCCAGGCTCCTGGG

AAGGGGCTGGAGTGGGTCTCAGCTATTTATACTAGTGGTAATTCTACAT

CTTACGCAGACTCCGTGAAGGGCCGGTTCACCATCTCCAGAGACAATTC

CAAGAACACGCTGTATCTGCAAATGAACAGCCTGAGAGCCGAGGACACG

GCCGTATATTACTGTGCGAAAAATGCTAGTAATTTTGACTACTGGGGCC

AGGGAACCCTGGTCACCGTCTCGAGCGGTGGAGGCGGTTCAGGCGGAGG

TGGCAGCGGCGGTGGCGGGTCGACGGACATCCAGATGACCCAGTCTCCA

TCCTCCCTGTCTGCATCTGTAGGAGACAGAGTCACCATCACTTGCCGGG

CAAGTCAGAGCATTAGCAGCTATTTAAATTGGTATCAGCAGAAACCAGG

GAAAGCCCCTAAGCTCCTGATCTATTCTGCATCCAATTTGCAAAGTGGG

GTCCCATCAAGGTTCAGTGGCAGTGGATCTGGGACAGATTTCACTCTCA

CCATCAGCAGTCTGCAACCTGAAGATTTTGCAACTTACTACTGTCAACA

GGGTTCTGATGCTCCTGCTACGTTCGGCCAAGGGACCAAGGTGGAAATC

AAACGGGCGGCCGCA

The nucleotide sequence may be natural, synthetic or recombinant. It may be double or single stranded, it may be DNA or RNA or combinations thereof. It may, for example, be cDNA, PCR product, genomic sequence or mRNA.

The nucleotide sequence may be codon optimised for production in the host/host cell of choice.

It mat be isolated, or as part of a plasmid, vector or host cell.

The percent identity between two nucleotide sequences can be determined by comparing a position in each sequence that may be aligned for purposes of comparison. Expression as a percentage of identity refers to a function of the number of identical nucleic acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g. default settings. ENTREZ is available through the National Center for Biotechnology Information, National Library of Medicine, National Institutes of Health, Bethesda, Md. The percent identity of two sequences may be determined by the GCG program with a gap weight of 1, e.g. each gap is weighted as if it were a single nucleotide mismatch between the two sequences.

The variant sequence may comprise on or more nucleotide substitutions, insertions or deletions. Insertions and deletions may be such that, overall, the majority of the coding sequence is "in-frame" with reference to SEQ ID No. 12. Nucleotide substitutions may be "silent" such that the codon encodes the same amino acid due to the degeneracy in the genetic code.

Where nucleotide substitutions cause a change in the encoded amino acid sequence, these may be concentrated in the framework regions and linker region of the polypeptide (i.e. those portions shown in black and red respectively on FIG. 7B). The regions encoding the CDRs (corresponding to the portions shown in brown in FIG. 7B) may comprise relatively few mutations. The regions encoding the CDRs should only comprise mutations which affect the amino acids in positions corresponding to those shown in red in FIG. 6, i.e. those represented by amino acid X in SEQ ID No 1-4, and not the other CDR residues.

Vector

The term "vector" refers to a nucleic acid molecule capable of transporting another nucleic acid to which it has been linked. One type of vector is an episome, i.e., a nucleic acid capable of extra-chromosomal replication. Another type of vector is an integrative vector that is designed to recombine with the genetic material of a host cell. Vectors may be both autonomously replicating and integrative, and the properties of a vector may differ depending on the cellular context (i.e., a vector may be autonomously replicating in one host cell type and purely integrative in another host cell type). Vectors capable of directing the expression of expressible nucleic acids to which they are operatively linked are referred to as "expression vectors."

A plasmid is an extra-chromosomal DNA molecule separate from the chromosomal DNA which is capable of replicating independently of the chromosomal DNA. They are usually circular and double-stranded.

Plasmids may be used to express a protein in a host cell. For example a bacterial host cell may be transfected with a plasmid capable of encoding a particular protein, in order to express that protein. The term also includes yeast artificial chromosomes and bacterial artificial chromosomes which are capable of accommodating longer portions of DNA.

Host Cell

The present invention further provides cells and cell lines capable of producing the antigen-binding polypeptides of the invention. Representative host cells include bacterial, yeast, mammalian and human cells, such as CHO cells, HEK-293 cells, HeLa cells, CV-1 cells, and COS cells. Methods for generating a stable cell line following transformation of a heterologous construct into a host cell are known in the art. Representative non-mammalian host cells include insect cells (Potter et al. (1993) Int. Rev. Immunol. 10(2-3): 103-112). Antibodies may also be produced in transgenic animals (Houdebine (2002) Curr. Opin. Biotechnol. 13(6):625-629) and transgenic plants (Schillberg et al. (2003) Cell Mol. Life Sci. 60(3):433-45).

Therapeutic Method

The antigen binding polypeptide of the present invention may be used in the treatment of arthritis or rheumatic diseases.

Arthritis is a general term relating to diseases characterised by cute or chronic inflammation of one or more joints, usually accompanied by pain and stiffness, resulting from infection, trauma, degenerative changes, autoimmune disease, or other causes.

Osteoartritis, also known as degenerative arthritis or degenerative joint disease, is a group of mechanical abnormalities involving degradation of joints, including articular cartilage and subchondral bone. Symptoms may include joint pain, tenderness, stiffness, locking, and sometimes an effusion, A variety of causes—hereditary, developmental, metabolic, and mechanical—may initiate processes leading to loss of cartilage.

Rheumatoid arthritis (RA) is a chronic, systemic inflammatory disorder that may affect many tissues and organs, but principally attacks synovial joints. The process produces an inflammatory response of the synovium (synovitis) secondary to hyperplasia of synovial cells, excess synovial fluid, and the development of pannus in the synovium. The pathology of the disease process often leads to the destruction of articular cartilage and ankylosis of the joints. Rheumatoid arthritis can also produce diffuse inflammation in the lungs, pericardium, pleura, and sclera, and also nodular lesions, most common in subcutaneous tissue under the skin. Although the cause of rheumatoid arthritis is unknown, autoimmunity plays a pivotal role in both its chronicity and progression, and RA is considered as a systemic autoimmune disease.

The antigen-binding polypeptide of the present invention may be used alone in the treatment of arthritis. The antigen-binding polypeptide may have intrinsic anti-angiogenic activity, for example it may be capable blocking essential mediators of vascular proliferation. Examples of such agents currently in clinical trials are drugs capable of neutralizing anti-VEGF antibodies and antibodies directed against a VEGF receptor or the αvβ3 integrin.

Alternatively the antigen-binding polypeptide may be used as a complex, for example a conjugate, or in a combination therapy with another agent (see below).

Disruption of Vasculature

The present invention also relates to methods involving disruption of existing synovial microvasculature.

The method may involve targeting of an agent to the synovial microvasculature using an antigen-binding polypeptide according to the present invention, the agent being capable of disrupting the existing microvasculature.

In order to avoid damage to normal tissue and blood vessels, the agent may be selectively activatable, so that it may be activated in situ after targeting to the synovial microvasculature. For example, the agent may be photosensitive and activated by light; or the agent may comprise a magnetic nanoparticle and be activated by a magnetic field.

Combination Therapies

The antigen-binding polypeptide of the present invention, or a complex of conjugate thereof, may be used in combination with another therapy. The two therapeutic agents may be for separate, subsequent or simultaneous administration.

The other therapy may comprise a therapeutic cytokine, an anti-angiogenic agent or an anti-rheumatic drug, as described above.

The antigen-binding polypeptide of the present invention may be used in combination another recombinant antibody used for the treatment of arthritis.

Currently, there are several recombinant antibodies in use for treatment of Rheumatoid Arthitis, targeting a range of cytkines, T cells and B cells. Since the initial approval of Etanercept, and shortly thereafter Infliximab, three additional TNF-neutralizing antibodies (Adalimumab, Certulizumab pegol and Golimumab) have been approved. Further, recombinant antibodies targeting T-cell [and/or dendritic cell], (Abatacept), B-cells, (Rituximab), and the receptor for cytokine IL-6, (Tocilizumab) have also been approved by the FDA for treatment of RA (Taylor and Feldmann 2009; Isaacs 2009 both as above).

The other treatment may involve blocking a tumor necrosis factor (TNF) pathway. TNF promotes the inflammatory response, which in turn causes many of the clinical problems associated with autoimmune disorders such as rheumatoid arthritis.

Inhibition of TNF can be achieved with a monoclonal antibody such as infliximab (Remicade), adalimumab (Humira), certolizumab pegol (Cimzia), and golimumab (Simponi), or with a circulating receptor fusion protein such as etanercept (Enbrel). While most clinically useful TNF inhibitors are monoclonal antibodies, some are simple molecules such as xanthine derivatives (e.g. pentoxifylline) and Bupropion.

Use of vascular targeted therapy in conjunction with second generation, recombinant TNF-α blockade therapeutics may prove more efficacious in treatment of RA than currently possible with a single immunotherapeutic agent.

Kits

The present invention also provides a kit comprising an antigen-binding polypeptide in accordance with the first aspect of the invention, or complex or conjugate thereof.

The kit may also comprise an agent for associating with the antigen-binding polypeptide prior to administration to a subject. The associated agent/antigen-binding polypeptide may then be targeted to the synovial microvasculature upon administration to the subject.

Where the antigen-binding polypeptide is for diagnostic use, the kit may also comprise further imaging reagents and/or apparatus.

Where the kit is for use in a combination therapy, the kit may also comprise a second therapeutic agent for simultaneous, subsequent or separate administration.

Imaging

The antigen-binding polypeptide may be used in imaging applications, for example in imaging the vasculature of arthritic joints.

To date, only few good-quality markers of angiogenesis, either on endothelial cells or in the modified ECM, are known. The biggest problem with many of the markers is that they lack sufficient specific expression or significant upregulation in tissues undergoing angiogenesis.

Some integrins, in particular αvβ3 and αvβ5, have been proposed both as markers and as functional mediators of angiogenesis in tumors and in ocular neovascular disorders. Expression of integrin αvβ3 was also shown to be increased in synovial blood vessels from patients with rheumatoid arthritis. However, in recent immunohistochemical studies, the vasculature in apparently normal tissue as well as several extravascular cell types were shown to stain positive for αvβ3, even though at lower intensity than in tissues undergoing angiogenesis.

Many recent studies have described endoglin (CD105), a component of the transforming growth factor-β receptor complex, as an attractive marker of neovascularization. Endoglin shows considerably increased expression on proliferating endothelium, but it also weakly stains endothelial cells in the majority of normal, healthy adult tissues of both human and mouse origin. Several monoclonal antibodies to endoglin have been characterized and have recently been tested as targeting agents for therapy and imaging of tumors. Unexpectedly, the targeting results obtained in mice were relatively modest, in spite of the accessible localization of the antigen on endothelial cells.

There is thus a need for improved agents for imaging the microvasculature of arthritic joints.

The antigen-binding polypeptide of the invention may be labelled for imaging techniques, with, for example a fluorescent or radioactive label.

In vivo imaging techniques using antibodies are well known in the art, including bioluminescence imaging (BLI) and biofluorescence imaging (BFI).

Diagnostic Methods

The present invention also provides a method for diagnosing a disease using an antigen-binding polypeptide according to the first aspect of the invention.

The present invention also provides a method for monitoring the progression of a disease and a method for evaluating the efficacy of a drug treatment using an antigen-binding polypeptide according to the first aspect of the invention.

The disease may be associated with a change, for example an increase, in the synovial microvasculature. The disease may be a form of arthritis, such as osteoarthritis or rheumatoid arthritis.

As explained in the background section, synovial angiogenesis is likely to precede other pathological features of RA, so the antigen-binding polypeptide of the present invention may be useful for the diagnosis of RA at an early stage, prior to the appearance of other symptoms.

The method may involve imaging the synovial microvasculature of a joint of the patient at one or a plurality of time points.

Targeting Method

The present invention also provides a method for targeting an agent to the synovial microvasculature which comprises the step of associating the agent with an antigen binding polypeptide according to the present invention in vitro.

The association may be such that when the associated agent/antigen-binding polypeptide is administered to an arthritis patient the agent is targeted to the synovial microvasculature. The agent may then accumulate selectively in neovascular sites.

The agent may, for example, be conjugated to the antigen-binding polypeptide.

The invention will now be further described by way of Examples, which are meant to serve to assist one of ordinary skill in the art in carrying out the invention and are not intended in any way to limit the scope of the invention.

EXAMPLES

Example 1

In Vivo Phage Display Selection of scFv Antibody Clones

The present inventors employed a synovial xenograft model in SCID mice in an in vivo phage display screen of the Tomlinson library in order to generate scFv antibody clones with specificity to the human synovial vasculature harboured within the xenografts.

The native Tomlinson library phage was injected via the tail vein and allowed to circulate for 15 minutes. Non-specific unbound phage was removed from the circulation by cardiac perfusion of the animal with normal saline. The synovial transplant was then extracted from the animal and processed for phage recovering and titration. Skin tissue xenografts carried by the mice simultaneously, were used as control tissue for the screen. The recovered phage from the synovial graft only was then amplified in TG1 *E. coli*, rescued, and prepared for subsequent rounds of in vivo selection. This process of affinity selection was repeated a further three rounds in order to enrich for antibodies with synovial specificity.

Example 2

Reactivity of scFv A7 with Human Synovial Tissue

Using immunohistological analysis the present inventors have demonstrated that scFv A7 exhibits specific reactivity with the microvasculature of Osteoarthritis and Rheumatoid Arthritis synovial tissue (FIG. 2).

Example 3

Identification of the Target Cell Type for scFv A7 within Synovial Microvasculature In order to specifically determine which cell types within the microvasculature are able to react with this antibody, the present inventors performed dual staining of RA synovial tissue using scFv A7 together with the endothelial specific markers Von Willebrand Factor (vWF) and CD 31, and the pericyte specific marker NG2. The results demonstrate clearly that dual staining of this tissue with scFv A7 and the pericyte marker NG2, shows complete overlap in the pattern of cellular staining observed demonstrating that scFV A7 has reactivity with pericytes and stromal component of the microvasculature of RA synovial tissue (FIG. 3). Components of the stromal compartment of the microvasculature are attractive for antibody based targeting applications, since this compartment is stable and present in abundance.

Example 4

In Vivo Targeting of Synovial Tissue by scFv A7

In order to confirm the specificity of reactivity of soluble scFv A7 in vivo, the ability of iodinated scFv A7 to target human synovial tissue xenografts in vivo was examined. The data demonstrate that at 4 hrs post injection, radiolabelled scFv A7 exhibits a three-fold preferential binding capacity to human synovium as opposed to human skin transplanted in SCID mice, retaining the synovial specificity of its parental phage clone. Further, despite an apparent fall in activity of scFv A7 in the synovium at 24 hrs, this tissue still maintains a significant differential in reactivity when compared to skin (FIG. 4).

Example 5

Specificity of Reactivity of scFv A7

In order to examine the specificity of reactivity of scFv A7 the inventors examined reactivity of this antibody with a range of normal human tissues using a whole body, normal survey tissue array. The data presented in FIG. 5 demonstrate that scFv A7 does not exhibits detectable reactivity with vital organs such as heart, lung, liver, pancreas, cerebral cortex and components of the digestive tract. Additionally, the antibody shows no reactivity with lymph, thymus, adrenal gland ovary and testis, further confirming its exquisite synovial tissue specificity.

Example 6 scFv A7 Reactivity with Normal Human Synovium

Having established that scFv A7 does not exhibit reactivity with the cellular components nor the microvasculature of a comprehensive range of normal tissues, the studies of specificity of scFv A7 reactivity with normal tissue were extended by examining reactivity of this antibody with the microvasculature of normal human synovial tissue. To do this, normal human synovial tissue was obtained from subjects undergoing joint arthroscopy for prolonged, unexplained knee pain that did not develop into arthritic conditions during a 5 years follow up survey. The results presented in FIG. 8 are representative of eleven samples and demonstrate that the microvasculature found in normal human synovium as detected by vWF reactivity, contains a stromal vascular component as detected by α smooth muscle actin reactivity. However, scFv A7 shows no reactivity with the microvasculature found in these synovium samples.

Example 7 scFv A7 Reactivity with Tissues from Other Inflammatory Disease

In order to establish whether the reactivity of scFv A7 is specific to the microvasculature of arthritic synovium or, a common feature of neovasculogenesis related to the presence of inflammation, we examined scFv A7 staining in tissue samples from patients with Crohn's disease (n=7) and psoriasis (n=5), where the presence of microvasculature was detected using anti-human vWF. The results presented in FIG. 9 demonstrate that scFv exhibits no detectable reactivity with the microvasculature found in either Crohn's or psoriatic tissues.

These results demonstrate that the target epitope for scFv A7 is absent from normal human tissues and microvasculature and is not expressed in the neovasculogenesis seen in inflammatory conditions. Together these results further support the conclusion that scFv A7 is specific for the microvasculature found in arthritic synovium.

Methods and Materials

ScFv Phage Library

The Human Single Fold scFv Libraries I+J (Tomlinson I+J) were obtained from the MRC (Medical Research Council) Resource Centre (Cambridge, UK) and selection performed according to the supplier's instructions (on line at: http://www.lifesciences.sourcebioscience.com/clone-products/proteomic-resources/human-single-fold-scfv-libraries-i-plus-j.aspx).

The Tomlinson I+J libraries are semi synthetic and based on a single human frame-work for VH (V3-23/DP-47 and JH4b) and Vk(O12/O2/DPK9 and Jk1), which encodes the most common human canonical structure. The CDR3 of the heavy chain is designed to be as short as possible yet still able to form an antigen binding surface. Additionally, CDR1 regions are kept constant whilst side-chain diversity is incorporated in CDR3 and CDR2 regions at positions, which make contacts to the antigens and are highly diverse in their mature native repertoire. The size of both libraries is about $1.4 \times 10^8$ and VH germline gene DP47 confers binding to Protein A.

Human Tissue Transplantation into SCID Mice

Beige SCID CB-17 mice aged 4-10 weeks were used in this study. Human tissues (synovium and skin) were transplanted subcutaneously in a dorsal position distal to the shoulder joints (two transplants per animal) as previously described (Wahid, Blades et al. 2000 Clin Exp Immunol 122:133-142). Mice were inspected daily and animal work was performed under a Project License (PPL 70-6109).

Human synovial tissue was obtained from patients with RA or Osteoarthritis (OA) undergoing joint replacement. Human skin tissue was obtained from patient undergoing cosmetic surgery. Informed consent was obtained from individual patients. Additionally, ethical approval to utilise human synovial and skin tissue for research purposes was obtained from the Ethics Committee of King's College Hospital (LREC n 05/Q0703/198).

In Vivo Selection of Synovium Specific Phage

Synovial specific phage was isolated following four rounds of enrichment in SCID mice carrying human arthritic synovial tissue and skin tissue xenografts, in an experimental model similar to the one previously described for a peptide library (Lee, Buckley et al. 2002 Arthritis Rheum 46:2109-2120). Briefly, four weeks post-transplantation with human synovial and skin tissue, $10^{11}$ tu (transforming units) of Tomlinson phage library made up in 200 µl of sterile saline were injected into the tail vein of SCID mice. The phage was allowed to circulate for 15 min, after which the animal was terminally anaesthetized. Non-specific unbound phage was removed from the circulation by cardiac perfusion of the animal with normal saline. The transplants (and on occasion mouse organs) were then removed and processed for phage recovery (using Trypsin) and titration. The recovered phage from the synovial grafts only, were amplified in TG1 E. coli, rescued and prepared for subsequent rounds of in vivo selection. Integrity of the scFv fragment expressed by the phage particles from the last round of selection was assessed by PCR. Clones that retained expression of full scFv fragment were then rescued for expression of soluble scFv protein.

In Vivo Localization of scFv A7 Phage scFv A7 phage clone was injected into two SCID mice bearing xenografts of human synovial and skin tissue, at $10^{11}$ tu, four weeks post transplantation. Phage particles were allowed to circulate for 15 min. after which time, the animals were perfused and the phage numbers retained in the two grafts determined by titration of the homogenised eluate. The differential phage localisation between the skin and synovium grafts, were subsequently quantified.

Sequencing of scFv Genes

Selected clones from the final round of enrichment were sequenced to determine the DNA sequences encoding the scFv inserts of isolated phage. Sequencing of scFv clones was performed using scFv-insert-specific primers LMB3 (CAG GAA ACA GCT ATG AC) and pHEN seq (CTA TGC GGC CCC ATT CA). Sequencing was performed using Big Dye® Terminator v3.1 Cycle Sequencing kit (Applied Biosystems) on an ABI PRISM 3130 Genetic analyzer.

Production of Soluble scFv Antibody Fragments scFv fragments rescued from the phage in the last round of selection were expressed in HB2151 E. coli for production of soluble scFv fragments in the supernatant. The efficiency of scFv protein production by each clone was assessed in a monoclonal ELISA. Subsequently, scFv protein was purified from culture supernatant by affinity chromatography using Protein A Sepharose Fast Flow Resin (GE Healthcare). Purified antibodies were analyzed by SDS-PAGE and size-exclusion chromatography on Superdex 75 HR10/30 columns (Amersham Biosciences), Soluble scFv A7 was purified as a monomeric protein at yields of 0.5-1 mg/ml.

Biotinylation of scFv Antibody Fragments

ScFv antibodies were biotinylated using the EZ-Link Sulfo-NHS-SS-Biotinylation kit (Perbio, Cramlington UK). Briefly, the desired scFv concentration to be biotinylated was diluted in 0.5-2 ml PBS, added to 20-fold molar excess of 10 mM Sulfo-NHS-SS-Biotin and incubated on ice for 1 hr. Biotinylated protein was subsequently isolated using desalting columns according to the manufacturers instructions.

Iodination of scFv Antibody Fragments scFv antibody fragments were radiolabeled with $\text{Na}^{125}\text{I}$ using the Iodogen method. Pierce Iodination Tubes precoated with Iodogen were used according to the manufacturer's instructions (Perbio, Cramlington UK). Typically, 25 ug of purified scFv in 150 ul were radiolabelled to specific activities of 0.15-0.2 MBq/ug. Efficiency of the labeling was tested by instant thin layer chromatography (typically over 90%) whilst purity of the labelled scFv was determined by reverse-phase HPLC.

In Vivo Localisation of Soluble scFv A7 Antibody Fragment

Two SCID mice bearing double xenografts of human arthritic synovial and skin tissues (two arthritic synovium and two human skin grafts per animal), were injected with 6 ug biotinylated scFv A7, four weeks post transplantation. Biotinylated anti-hen egg lysozyme antibody fragment, scFv HEL, was used as antibody negative control. The biotinylated antibody fragments were administered via the tail vein in a total volume of 200 µl and were allowed to circulate for 15 min. after which time the mice were perfused under terminal anaesthesia. The human grafts along with murine tissues were subsequently harvested and immediately snap frozen for histological examination. The tissue specific localization of soluble scFv A7 to the microvasculature of arthritic synovial tissue grafts was examined by immunohistochemical detection of biotinylated scFv A7 in tissue sections, using avidin-biotin-HRP (ABC-HRP) complex (Dako Ltd, Ely UK). Reactivity of scFv A7 added in vitro, was also examined in these samples.

In Vivo Targeting Capacity of Iodinated scFv A7 Antibody Fragment

Five double transplanted SCID mice (two arthritic synovium and two human skin grafts per animal) were injected with iodinated scFv antibody four weeks post transplantation. The injection dose per animal was a total volume of 200 µl made up in sterile saline, containing 1.25 µg of scFv with a total radioactivity of 0.2 Mbq. The labeled antibody fragments were administered via the tail vein. Mice were sacrificed at 4 hr and 24 hr post injection, and grafts as well as mouse organs collected for gamma counting. The results were subsequently corrected for tissue weight and background radioactivity in the blood pool, and expressed as percentage of the total injected dose. Iodinated scFv HEL was used s negative control antibody.

Immunohistochemical Analysis

Frozen sections of tissue were fixed in ice-cold acetone and stained with 1 ug biotinylated scFv A7. Paraffin embedded tissues were dewaxed and subsequently treated with Proteinase K (Dako Ltd, UK) for 4 min at room temperature for antigen retrieval. ScFv A7 was used at 4 ug and was detected through its biotin label using avidin-biotin-HRP (ABC-HRP) complex (Dako Ltd, UK). Presence of human blood vessels in the tissue sections was depicted using anti-human vWF (Dako) followed by an HRP-conjugated anti mouse antibody. Anti mouse CD 31 was used to detect mouse endothelial blood vessels in murine tissue. Slides were counterstained with haematoxylin, mounted with Depex mounting medium (Dako) and analysed using a light microscope (Olympus, Watford, UK).

Immunofluorescent Analysis

Frozen sections of tissue were fixed in ice-cold acetone prior to antibody staining. Biotinylated scFv A7 reactivity was detected by using Texas Red conjugated NeutrAvidin (Invitrogen). Anti human vWF (Dako), anti human CD 31 (Sigma) and anti NG2 antibody (Millipore) reactivity was detected using Alexa 488 or Alexa 594 (Invitrogen). Sections were subsequently mounted in the fluorescent mounting media Vectashield with DAPI (Vector Labs. UK.) for counterstaining nuclei, and examined using an Axioskop 2 microscope (Carl Zeiss Ltd, UK). Images were captured by an AxioCam digital colour camera using KS300 image analysis software (Zeiss, UK).

Assessment and Quantification of Human Vasculature within Tissue Grafts

In order to assess the degree of vascularisation of the human grafts, the human endothelial surface was determined immunohistologically using anti-human vWF. Briefly, human synovium and skin graft sections were stained with anti-vWF antibody and the volume fraction (Vv) of immunostained human vessels determined microscopically using a point counting method as previously described (Lee, Buckley et al. 2002 as above).

Statistics

Results are expressed as the mean and standard deviation (SD), or standard error of the mean (SEM). Parametric analyses were performed using the Graphpad Prism software (Graphpad Software, San Diego USA), commonly by unpaired two-tail t-test.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. An antibody or antigen binding fragment thereof which specifically targets the synovial microvasculature of arthritis patients and comprises:
   (i) the VH sequence as shown in SEQ ID NO: 9; and
   (ii) the VL sequence as shown in SEQ ID NO: 10.

2. The antibody or antigen binding fragment according to claim 1 which reacts with the stromal compartment of the microvasculature.

3. The antibody or antigen binding fragment according to claim 1 which binds to pericytes.

4. The antibody or antigen binding fragment according to claim 1 which exhibits perivascular reactivity.

5. The antibody or antigen binding fragment according to claim 1 which is an scFv.

6. The antibody or antigen binding fragment according to claim 1 which is a human antibody.

7. The antibody or antigen binding fragment according to claim 1 which specifically targets the synovial microvasculature of osteoarthritis and/or rheumatoid arthritis patients.

8. The antibody or antigen binding fragment according to claim 1, which is conjugated to one or more of the following: a therapeutic cytokine, an anti-angiogenic agent, an anti-rheumatic drug a photosensitive agent or a magnetic nanoparticle.

9. The antibody or antigen binding fragment according to claim 1 which is a purified antibody or antigen binding fragment.

10. The antibody or antigen binding fragment according to claim 9 which is a recombinantly produced, soluble antibody or antigen binding fragment.

11. A biopharmaceutical that comprises the antibody or antigen binding fragment according to claim 10.

12. A method for treating arthritis in a subject, which comprises the step of administering to the subject the antibody or antigen binding fragment according to claim 1 conjugated to one or more of the following: a therapeutic cytokine, an anti-angiogenic agent, an anti-rheumatic drug, a photosensitive agent or a magnetic nanoparticle.

13. A method for treating arthritis in a subject, which comprises the following steps:
   (i) administering the antibody or antigen binding fragment according to claim 1, conjugated to a photosensitive agent, to a subject;

(ii) targeting the conjugate to the synovial vasculature of a joint;
(iii) applying light to the joint in order to activate the photosensitive agent within the synovial vasculature.

14. A method according to claim 13, wherein activation of the agent leads to the disruption of existing vasculature.

15. A method according to claim 13, wherein the antibody or antigen binding fragment is an scFv.

16. A method for treating arthritis in a subject, which comprises the following steps:
   (i) administering the antibody or antigen binding fragment according to claim 1, conjugated to a magnetic nanoparticle, to a subject;
   (ii) targeting the conjugate to the synovial vasculature of a joint;
   (iii) applying a magnetic field to the joint in order to activate the magnetic nanoparticle within the synovial vasculature.

17. A method for producing an antibody conjugate which, when administered to a patient, is targeted to the synovial microvasculature, which method comprises the step of conjugating the antibody or antigen binding fragment according to claim 1 to an agent.

18. A method for targeting an agent to the synovial microvasculature which comprises:
   administering to an arthritis patient the antibody or antigen binding fragment according to claim 1 conjugated to the agent.

* * * * *

SEQUENCE LISTING

```
<160> NUMBER OF SEQ ID NOS: 24

<210> SEQ ID NO 1
<211> LENGTH: 17
<212> TYPE: PRT
<213> ORGANISM: Artificial Sequence
<220> FEATURE:
<223> OTHER INFORMATION: Complementarity determining region (CDR)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(17)
<223> OTHER INFORMATION: Xaa can be any naturally occurring amino acid

<400> SEQUENCE: 1

Ala Xaa Tyr Thr Ser Xaa Asn Ser Xaa Ser Xaa Xaa Xaa Xaa Xaa Xaa
1               5                   10                  15
Xaa

<210> SEQ ID NO 2
<211> LENGTH: 7
<212> TYPE: PRT
<213> ORGANISM: Artificial Sequence
<220> FEATURE:
<223> OTHER INFORMATION: Complementarity determining region (CDR)
<220> FEATURE:
<221> NAME/KEY: misc_feature
<222> LOCATION: (5)..(7)
<223> OTHER INFORMATION: Xaa can be any naturally occurring amino acid

<400> SEQUENCE: 2

Asn Ala Ser Asn Xaa Xaa Xaa
```

```
1               5

<210> SEQ ID NO 3
<211> LENGTH: 7
<212> TYPE: PRT
<213> ORGANISM: Artificial Sequence
<220> FEATURE:
<223> OTHER INFORMATION: Complementarity determining region (CDR)
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 3

Ser Xaa Xaa Asn Xaa Xaa Xaa
1               5

<210> SEQ ID NO 4
<211> LENGTH: 9
<212> TYPE: PRT
<213> ORGANISM: Artificial Sequence
<220> FEATURE:
<223> OTHER INFORMATION: Complementarity determining region (CDR)
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 4

Xaa Xaa Gly Ser Asp Ala Xaa Ala Xaa
1               5

<210> SEQ ID NO 5
<211> LENGTH: 17
<212> TYPE: PRT
<213> ORGANISM: Artificial Sequence
<220> FEATURE:
<223> OTHER INFORMATION: Complementarity determining region (CDR)

<400> SEQUENCE: 5

Ala Ile Tyr Thr Ser Gly Asn Ser Thr Ser Tyr Ala Asp Ser Val Lys
1               5                   10                  15

Gly

<210> SEQ ID NO 6
<211> LENGTH: 7
<212> TYPE: PRT
<213> ORGANISM: Artificial Sequence
<220> FEATURE:
<223> OTHER INFORMATION: Complementarity determining region (CDR)

<400> SEQUENCE: 6

Asn Ala Ser Asn Phe Asp Tyr
1               5

<210> SEQ ID NO 7
<211> LENGTH: 7
```

```
<212> TYPE: PRT
<213> ORGANISM: Artificial Sequence
<220> FEATURE:
<223> OTHER INFORMATION: Complementarity determining region (CDR)

<400> SEQUENCE: 7

Ser Ala Ser Asn Leu Gln Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Complementarity determining region (CDR)

<400> SEQUENCE: 8

Gln Gln Gly Ser Asp Ala Pro Ala Thr
1               5

<210> SEQ ID NO 9
<211> LENGTH: 116
<212> TYPE: PRT
<213> ORGANISM: Artificial Sequence
<220> FEATURE:
<223> OTHER INFORMATION: Antigen binding polypeptide VL region

<400> SEQUENCE: 9

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Tyr Thr Ser Gly Asn Ser Thr Ser Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asn Ala Ser Asn Phe Asp Tyr Trp Gly Gln Gly Thr
            100                 105                 110

Leu Val Thr Val
        115

<210> SEQ ID NO 10
<211> LENGTH: 112
<212> TYPE: PRT
<213> ORGANISM: Artificial Sequence
<220> FEATURE:
<223> OTHER INFORMATION: Antigen binding polypeptide VH region

<400> SEQUENCE: 10

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ser Ala Ser Asn Leu Gln Ser Gly Val Pro Ser Arg Phe Ser
    50                  55                  60
```

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Gly Ser Asp Ala Pro
                85                  90                  95

Ala Thr Phe Gly Gln Gly Thr Lys Val Glu Ile Lys Arg Ala Ala Ala
            100                 105                 110

<210> SEQ ID NO 11
<211> LENGTH: 245
<212> TYPE: PRT
<213> ORGANISM: Artificial Sequence
<220> FEATURE:
<223> OTHER INFORMATION: Antigen binding polypeptide (scFv)

<400> SEQUENCE: 11

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Tyr Thr Ser Gly Asn Ser Thr Ser Tyr Ala Asp
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asn Ala Ser Asn Phe Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Thr Asp Ile Gln Met Thr Gln Ser Pro Ser Ser
130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ser Ala Ser Asn Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Gly Ser Asp Ala Pro Ala Thr Phe Gly Gln Gly Thr Lys Val Glu Ile
225                 230                 235                 240

Lys Arg Ala Ala Ala
            245

<210> SEQ ID NO 12
<211> LENGTH: 750
<212> TYPE: DNA
<213> ORGANISM: Artificial Sequence
<220> FEATURE:
<223> OTHER INFORMATION: Nucleotide sequence capable of encoding an
      antigen binding polypeptide

<400> SEQUENCE: 12
gcggcccagc cggccatggc cgaggtgcag ctgttggagt ctggggggagg cttggtacag    60

```
cctgggggt ccctgagact ctcctgtgca gcctctggat tcacctttag cagctatgcc    120
atgagctggg tccgccaggc tcctgggaag gggctggagt gggtctcagc tatttatact   180
agtggtaatt ctacatctta cgcagactcc gtgaagggcc ggttcaccat ctccagagac   240
aattccaaga cacgctgta tctgcaaatg aacagcctga gagccgagga cacggccgta    300 [sic, see image]

tattactgtg cgaaaaatgc tagtaattt gactactggg gccagggaac cctggtcacc    360
gtctcgagcg gtggaggcgg ttcaggcgga ggtggcagcg gcggtggcgg gtcgacggac   420
atccagatga cccagtctcc atcctccctg tctgcatctg taggagacag agtcaccatc   480
acttgccggg caagtcagag cattagcagc tatttaaatt ggtatcagca gaaaccaggg   540
aaagccccta agctcctgat ctattctgca tccaatttgc aaagtggggt cccatcaagg   600
ttcagtggca gtggatctgg gacagatttc actctcacca tcagcagtct gcaacctgaa   660
gattttgcaa cttactactg tcaacagggt tctgatgctc ctgctacgtt cggccaaggg   720
accaaggtgg aaatcaaacg ggcggccgca                                   750
```

<210> SEQ ID NO 13
<211> LENGTH: 17
<212> TYPE: DNA
<213> ORGANISM: Artificial Sequence
<220> FEATURE:
<223> OTHER INFORMATION: Primer

<400> SEQUENCE: 13
caggaaacag ctatgac    17

<210> SEQ ID NO 14
<211> LENGTH: 17
<212> TYPE: DNA
<213> ORGANISM: Artificial Sequence
<220> FEATURE:
<223> OTHER INFORMATION: Primer

<400> SEQUENCE: 14
ctatgcggcc ccattca    17

<210> SEQ ID NO 15
<211> LENGTH: 17
<212> TYPE: PRT
<213> ORGANISM: Artificial Sequence
<220> FEATURE:
<223> OTHER INFORMATION: Complementarity deteremining region (CDR)
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(17)
<223> OTHER INFORMATION: Xaa can be any naturally occurring amino acid

<400> SEQUENCE: 15

Ala Ile Tyr Thr Ser Xaa Asn Ser Xaa Ser Xaa Xaa Xaa Xaa Xaa Xaa
1               5                   10                  15

Xaa

<210> SEQ ID NO 16
<211> LENGTH: 17

-continued

```
<212> TYPE: PRT
<213> ORGANISM: Artificial Sequence
<220> FEATURE:
<223> OTHER INFORMATION: Complementarity determining region (CDR)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(17)
<223> OTHER INFORMATION: Xaa can be any naturally occurring amino acid

<400> SEQUENCE: 16

Ala Xaa Tyr Thr Ser Gly Asn Ser Xaa Ser Xaa Xaa Xaa Xaa Xaa Xaa
1               5                   10                  15

Xaa

<210> SEQ ID NO 17
<211> LENGTH: 17
<212> TYPE: PRT
<213> ORGANISM: Artificial Sequence
<220> FEATURE:
<223> OTHER INFORMATION: Complementarity determining region (CDR)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(17)
<223> OTHER INFORMATION: Xaa can be any naturally occurring amino acid

<400> SEQUENCE: 17

Ala Xaa Tyr Thr Ser Xaa Asn Ser Thr Ser Xaa Xaa Xaa Xaa Xaa Xaa
1               5                   10                  15

Xaa

<210> SEQ ID NO 18
<211> LENGTH: 17
<212> TYPE: PRT
<213> ORGANISM: Artificial Sequence
<220> FEATURE:
<223> OTHER INFORMATION: Complementarity determining region (CDR)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(17)
<223> OTHER INFORMATION: Xaa can be any naturally occurring amino acid

<400> SEQUENCE: 18

Ala Xaa Tyr Thr Ser Xaa Asn Ser Xaa Ser Tyr Xaa Xaa Xaa Xaa Xaa
1               5                   10                  15
```

Xaa

<210> SEQ ID NO 19
<211> LENGTH: 17
<212> TYPE: PRT
<213> ORGANISM: Artificial Sequence
<220> FEATURE:
<223> OTHER INFORMATION: Complementarity determining region (CDR)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid

<400> SEQUENCE: 19

Ala Xaa Tyr Thr Ser Xaa Asn Ser Xaa Ser Xaa Ala Xaa Xaa Xaa Xaa
1               5                   10                  15

Xaa

<210> SEQ ID NO 20
<211> LENGTH: 17
<212> TYPE: PRT
<213> ORGANISM: Artificial Sequence
<220> FEATURE:
<223> OTHER INFORMATION: Complementarity determining region (CDR)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid

<400> SEQUENCE: 20

Ala Xaa Tyr Thr Ser Xaa Asn Ser Xaa Ser Xaa Xaa Asp Xaa Xaa Xaa
1               5                   10                  15

Xaa

<210> SEQ ID NO 21
<211> LENGTH: 17
<212> TYPE: PRT
<213> ORGANISM: Artificial Sequence
<220> FEATURE:

```
<223> OTHER INFORMATION: Complementarity determining region (CDR)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid

<400> SEQUENCE: 21

Ala Xaa Tyr Thr Ser Xaa Asn Ser Xaa Ser Xaa Xaa Xaa Ser Xaa Xaa
1               5                   10                  15

Xaa

<210> SEQ ID NO 22
<211> LENGTH: 17
<212> TYPE: PRT
<213> ORGANISM: Artificial Sequence
<220> FEATURE:
<223> OTHER INFORMATION: Complementarity determining region (CDR)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(14)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid

<400> SEQUENCE: 22

Ala Xaa Tyr Thr Ser Xaa Asn Ser Xaa Ser Xaa Xaa Xaa Xaa Val Xaa
1               5                   10                  15

Xaa

<210> SEQ ID NO 23
<211> LENGTH: 17
<212> TYPE: PRT
<213> ORGANISM: Artificial Sequence
<220> FEATURE:
<223> OTHER INFORMATION: Complementarity determining region (CDR)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
```

```
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 23

Ala Xaa Tyr Thr Ser Xaa Asn Ser Xaa Ser Xaa Xaa Xaa Xaa Xaa Lys
1               5                   10                  15

Xaa

<210> SEQ ID NO 24
<211> LENGTH: 17
<212> TYPE: PRT
<213> ORGANISM: Artificial Sequence
<220> FEATURE:
<223> OTHER INFORMATION: Complementarity determining region (CDR)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(16)
<223> OTHER INFORMATION: Xaa can be any naturally occurring amino acid

<400> SEQUENCE: 24

Ala Xaa Tyr Thr Ser Xaa Asn Ser Xaa Ser Xaa Xaa Xaa Xaa Xaa Xaa
1               5                   10                  15

Gly
```